(12) United States Patent
Katsumoto

(10) Patent No.: US 10,493,446 B2
(45) Date of Patent: Dec. 3, 2019

(54) FLOW CHANNEL DEVICE, ANALYSIS APPARATUS, AND FLUID APPARATUS

(71) Applicant: Sony Corporation, Tokyo (JP)

(72) Inventor: Yoichi Katsumoto, Tokyo (JP)

(73) Assignee: Sony Corporation, Tokyo (JP)

( * ) Notice: Subject to any disclaimer, the term of this patent is extended or adjusted under 35 U.S.C. 154(b) by 696 days.

(21) Appl. No.: 14/786,255

(22) PCT Filed: Apr. 14, 2014

(86) PCT No.: PCT/JP2014/002105
§ 371 (c)(1),
(2) Date: Oct. 22, 2015

(87) PCT Pub. No.: WO2014/181500
PCT Pub. Date: Nov. 13, 2014

(65) Prior Publication Data
US 2016/0082432 A1    Mar. 24, 2016

(30) Foreign Application Priority Data

May 8, 2013    (JP) .................................. 2013-098215

(51) Int. Cl.
*B01L 1/00*    (2006.01)
*B01L 3/00*    (2006.01)
(Continued)

(52) U.S. Cl.
CPC ........... *B01L 3/502* (2013.01); *B01L 3/50273* (2013.01); *B01L 3/502715* (2013.01);
(Continued)

(58) Field of Classification Search
CPC ....... B01L 2200/027; B01L 2200/0621; B01L 2200/10; B01L 2200/16; B01L 2300/0645;
(Continued)

(56) References Cited

U.S. PATENT DOCUMENTS

| 7,069,952 B1 | 7/2006 | McReynolds et al. |
| 8,147,770 B2 * | 4/2012 | Banerjee ........... B01L 3/502738 422/255 |

(Continued)

FOREIGN PATENT DOCUMENTS

| CN | 101301632 A | 11/2008 |
| JP | 2005-037368 A | 2/2005 |

(Continued)

OTHER PUBLICATIONS

International Search Report and Written Opinion and English translation thereof dated Jul. 8, 2014 in connection with International Application No. PCT/JP2014/002105.

(Continued)

*Primary Examiner* — Dean Kwak
(74) *Attorney, Agent, or Firm* — Wolf, Greenfield & Sacks, P.C.

(57) ABSTRACT

[Solving Means] A flow channel device includes a vessel layer and a flow channel layer. The vessel layer includes an injection vessel section into which a fluid including a sample is injected and a collection vessel section that collects the fluid. The flow channel layer includes a flow channel connected to the injection vessel section and the collection vessel section and is bonded to the vessel layer.

14 Claims, 14 Drawing Sheets

(51) Int. Cl.
*G01N 15/14* (2006.01)
*G01N 27/02* (2006.01)
*G01N 15/10* (2006.01)
*G01N 15/12* (2006.01)

(52) U.S. Cl.
CPC ..... *G01N 15/1459* (2013.01); *G01N 15/1484* (2013.01); *G01N 27/02* (2013.01); *B01L 2200/027* (2013.01); *B01L 2200/0621* (2013.01); *B01L 2200/10* (2013.01); *B01L 2200/16* (2013.01); *B01L 2300/0645* (2013.01); *B01L 2300/0654* (2013.01); *B01L 2300/0816* (2013.01); *B01L 2300/0867* (2013.01); *B01L 2300/0874* (2013.01); *B01L 2300/0877* (2013.01); *B01L 2300/0887* (2013.01); *B01L 2400/0421* (2013.01); *B01L 2400/0487* (2013.01); *B01L 2400/06* (2013.01); *B01L 2400/0677* (2013.01); *G01N 2015/1006* (2013.01); *G01N 2015/1263* (2013.01); *G01N 2015/149* (2013.01)

(58) Field of Classification Search
CPC ..... B01L 2300/0816; B01L 2300/0867; B01L 2300/0874; B01L 2300/0877; B01L 2300/0887; B01L 2400/0421; B01L 2400/0487; B01L 2400/06; B01L 2400/0677; B01L 3/502; B01L 3/502715; B01L 3/50273
USPC ................. 422/502–505, 417, 568; 436/180
See application file for complete search history.

(56) References Cited

U.S. PATENT DOCUMENTS

| | | | |
|---|---|---|---|
| 9,429,276 B2* | 8/2016 | Katsumoto | ............... F17D 1/00 |
| 2002/0047003 A1* | 4/2002 | Bedingham | ........... B01L 3/5025 |
| | | | 219/388 |
| 2002/0196435 A1* | 12/2002 | Cohen | ............... B01L 3/502753 |
| | | | 356/246 |
| 2005/0054078 A1 | 3/2005 | Miller et al. | |
| 2009/0068760 A1 | 3/2009 | Nelson | |
| 2011/0003303 A1 | 1/2011 | Pagano et al. | |
| 2011/0008817 A1 | 1/2011 | Durack | |

FOREIGN PATENT DOCUMENTS

| | | |
|---|---|---|
| JP | 2007-511740 A | 5/2007 |
| JP | 2011-013208 A | 1/2011 |
| JP | 2012-530246 A | 11/2012 |
| WO | WO 2000/060352 A2 | 10/2000 |
| WO | WO 2005/026690 A2 | 3/2005 |
| WO | WO 2010/140706 A1 | 12/2010 |
| WO | WO 2010/144745 A2 | 12/2010 |

OTHER PUBLICATIONS

International Preliminary Report on Patentability and English translation thereof dated Nov. 19, 2015 in connection with International Application No. PCT/JP2014/002105.

Chinese Office Action dated Aug. 9, 2016 in connection with Chinese Application No. 2014800246654 and English translation thereof.

Extended European Search Report dated Dec. 1, 2016 in connection with European Application No. 14795205.5.

* cited by examiner

FLOW CHANNEL DEVICE, ANALYSIS APPARATUS, AND FLUID APPARATUS

CROSS-REFERENCE TO RELATED APPLICATIONS

This application is a National Stage of International Application No. PCT/JP2014/002105, filed in the Japanese Patent Office as a Receiving office on Apr. 14, 2014, which claims priority to Japanese Patent Application Number 2013-098215, filed in the Japanese Patent Office on May 8, 2013, each of which is hereby incorporated by reference in its entirety.

TECHNICAL FIELD

The present technique relates to a flow channel device where a fluid including a sample flows, and an analysis apparatus and fluid apparatus that use the flow channel device.

BACKGROUND ART

Patent Document 1 discloses a cartridge that is used for performing a chemical reaction of a sample. This cartridge is constituted of a substrate as a rigid body and a vessel as an elastic body, and a flow channel and two or more chambers coupled by the flow path are formed in the vessel. For example, the cartridge includes a chamber for accumulating two types of solutions, a reaction chamber in which the solutions are mixed to cause a reaction, and an effluent accommodation chamber. By rotating and moving a roller or the like and applying an external force to the elastic body of the cartridge, the elastic body is crushed and the solutions in the flow channel or chamber move (see, for example, paragraphs [0013] and [0016] in specification and FIGS. 2, 3, etc. in Patent Document 1).
Patent Document 1: Japanese Patent Application Laid-open No. 2005-37368

SUMMARY OF INVENTION

Problem to be Solved by the Invention

In the cartridge disclosed in Patent Document 1, the reactant needs to be extruded from a discharge port by a pressing force of the roller as shown in FIG. 18, for example. Therefore, the cartridge has poor workability when it is necessary to collect samples, which is disadvantageous.

An object of the present technique is to provide a flow channel device suited for tasks of a sample injection and collection, and a sorting apparatus and fluid apparatus that use the flow channel device.

Means for Solving the Problem

To attain the object described above, according to the present technique, there is provided a flow channel device including a vessel layer and a flow channel layer.

The vessel layer includes an injection vessel section into which a fluid including a sample is injected and a collection vessel section that collects the fluid; and The flow channel layer includes a flow channel connected to the injection vessel section and the collection vessel section and is bonded to the vessel layer.

Since the flow channel layer is bonded to the vessel layer and the injection vessel section and the collection vessel section are provided in the same vessel layer, the injection and collection of the fluid including the sample become simple, and workability is improved.

The injection vessel section may be formed by a through hole provided in the vessel layer while using a surface of the flow channel layer as a bottom or include a concave section provided in the vessel layer.

Alternatively, the collection vessel section may be formed by a through hole provided in the vessel layer while using a surface of the flow channel layer as a bottom or include a concave section provided in the vessel layer.

The collection vessel section may include a concave accumulation section provided in the through hole or the concave section. The collection vessel section may also include a collection vessel inflow channel connected to an outside area of the accumulation section in the through hole or the concave section. With this structure, in a case where the fluid flows into the collection vessel section from the flow channel, if the fluid flows to the outside area of the accumulation section via the collection vessel inflow channel, the sample included in the fluid sediments by a gravity to be accumulated in the accumulation section.

The flow channel of the flow channel layer may further include a collection vessel outflow channel that opposes the collection vessel inflow channel and is connected to the flow channel. The fluid that flows at a higher speed than the sinking sample is apt to travel toward the collection vessel outflow channel provided opposed to the collection vessel inflow channel and can therefore smoothly flow out of the collection vessel outflow channel.

The vessel layer may include a first inflow channel of a fluid not including the sample, the first inflow channel communicating an outside of the flow channel device and the flow channel of the flow channel layer with each other. Further, the flow channel of the flow channel layer may include a first flow channel connected to the first inflow channel, and an injection vessel inflow channel and an injection vessel outflow channel that are branched from the first flow channel and connected to the injection vessel section. With this structure, the fluid that has flown into the first flow channel via the first inflow channel can circumvent via the injection vessel inflow channel, the injection vessel section, and the injection vessel outflow channel. The fluid including the sample, that has flown out to the first flow channel via the injection vessel outflow channel, joins the fluid not including the sample, that is flowing through the first flow channel.

The injection vessel outflow channel may have a smaller flow channel cross-sectional area than the first flow channel and may be connected to the first flow channel at a center position of a width of the first flow channel in a direction orthogonal to a flowing direction of the fluid. With this structure, the fluid that has flown out of the injection vessel outflow channel joins the fluid flowing through the first flow channel to become a laminar flow, and the samples included in the fluid can be aligned.

The flow channel of the flow channel layer may include a narrowing channel and a second flow channel that is connected to the first flow channel via the narrowing channel and the collection vessel section. By proving the narrowing channel as described above, particles such as cells can be caused to pass through the narrowing channel as samples and analyzed.

The vessel layer may include a second inflow channel connected to the second flow channel. By the first flow channel and the second flow channel, a crossflow of the fluid can be formed.

The vessel layer may include an outflow channel that communicates the first flow channel and the outside of the flow channel device with each other.

The second flow channel of the flow channel layer may include a plurality of branched branch channels, and one of the plurality of branch channels may be connected to the collection vessel section. With this structure, the sample passes the selected one of the plurality of branch channels to be collected in the collection vessel section.

The flow channel layer may include an electrode pair provided in the flow channel while sandwiching the narrowing channel. With this structure, an electrical analysis of the sample becomes possible.

The flow channel layer may include an operation electrode section that is provided between the narrowing channel and the plurality of branch channels in the second flow channel and applies an electrophoretic force to the sample.

The vessel layer may include a first inflow channel and a second inflow channel for a fluid not including the sample, the first inflow channel and the second inflow channel communicating an outside of the flow channel device and the flow channel of the flow channel layer with each other. The flow channel of the flow channel layer may include a first flow channel connected to the first inflow channel and a second flow channel connected to the second inflow channel. The vessel layer may include a first outflow channel that communicates the first flow channel and the outside of the flow channel device with each other and a second outflow channel that communicates the second flow channel and the outside of the flow channel device with each other.

The flow channel device may further include a film-like seal member that is provided above the injection vessel section and the collection vessel section of the vessel layer. By a flexibility of the film-like seal member, when there are air bubbles in the injection vessel section, for example, an operator can seal the injection vessel section by extruding the air bubbles outside the flow channel device.

The flow channel device may further include a valve provided between the injection vessel section and the flow channel of the flow channel layer. With this structure, the injection vessel section and the flow channel can be secluded from each other.

The valve may be a water-soluble seal member. With this structure, the injection vessel section and the flow channel can be secluded and the fluid can be kept inside the injection vessel section for a predetermined time since the fluid including the sample is injected into the injection vessel section.

According to the present technique, there is provided an analysis apparatus including a flow channel device and an apparatus.

The flow channel device includes a vessel layer and a flow channel layer. The vessel layer includes an injection vessel section into which a fluid including a sample is injected and a collection vessel section that collects the fluid. The flow channel layer includes a flow channel connected to the injection vessel section and the collection vessel section and an electrode section provided at a predetermined position of the flow channel and is bonded to the vessel layer.

The apparatus includes a signal generation section that causes the electrode section to generate a voltage signal, and a measurement section that measures an electrical amount at the predetermined position when the sample passes the predetermined position.

According to another aspect of the present technique, there is provided an analysis apparatus including a flow channel device, a light irradiation section, and a detection section.

The flow channel device includes a vessel layer and a flow channel layer. The vessel layer includes an injection vessel section into which a fluid including a sample is injected and a collection vessel section that collects the fluid. The flow channel layer includes a flow channel connected to the injection vessel section and the collection vessel section and is bonded to the vessel layer.

The light irradiation section is capable of irradiating light onto the sample that passes a predetermined position of the flow channel of the flow channel layer.

The detection section detects at least one of fluorescent light and scattering light emitted from the sample due to the irradiation of light.

According to the present technique, there is provided a fluid apparatus including a flow channel device and a flow control mechanism.

The flow channel device includes a vessel layer and a flow channel layer. The vessel layer includes an injection vessel section into which a fluid including a sample is injected and a collection vessel section that collects the fluid. The flow channel layer includes a flow channel connected to the injection vessel section and the collection vessel section, an inlet of the flow channel, and an outlet of the flow channel and is bonded to the vessel layer.

The flow control mechanism is connected to each of the inlet and the outlet of the flow channel and controls a flow of the fluid flowing in the flow channel.

The vessel layer may include a first inflow channel and a second inflow channel for a fluid not including the sample, the first inflow channel and the second inflow channel communicating an outside of the flow channel device and the flow channel of the flow channel layer with each other. The flow channel of the flow channel layer may include a first flow channel connected to the first inflow channel and a second flow channel connected to the second inflow channel. The vessel layer may include a first outflow channel that communicates the first flow channel and the outside of the flow channel device with each other and a second outflow channel that communicates the second flow channel and the outside of the flow channel device with each other.

Effects of the Invention

As described above, according to the present technique, workability of a sample's injection and collection can be improved.

MODE FOR CARRYING OUT THE INVENTION

Hereinafter, an embodiment of the present technique will be described with reference to the drawings.

1. Flow Channel Device

Figure 1:
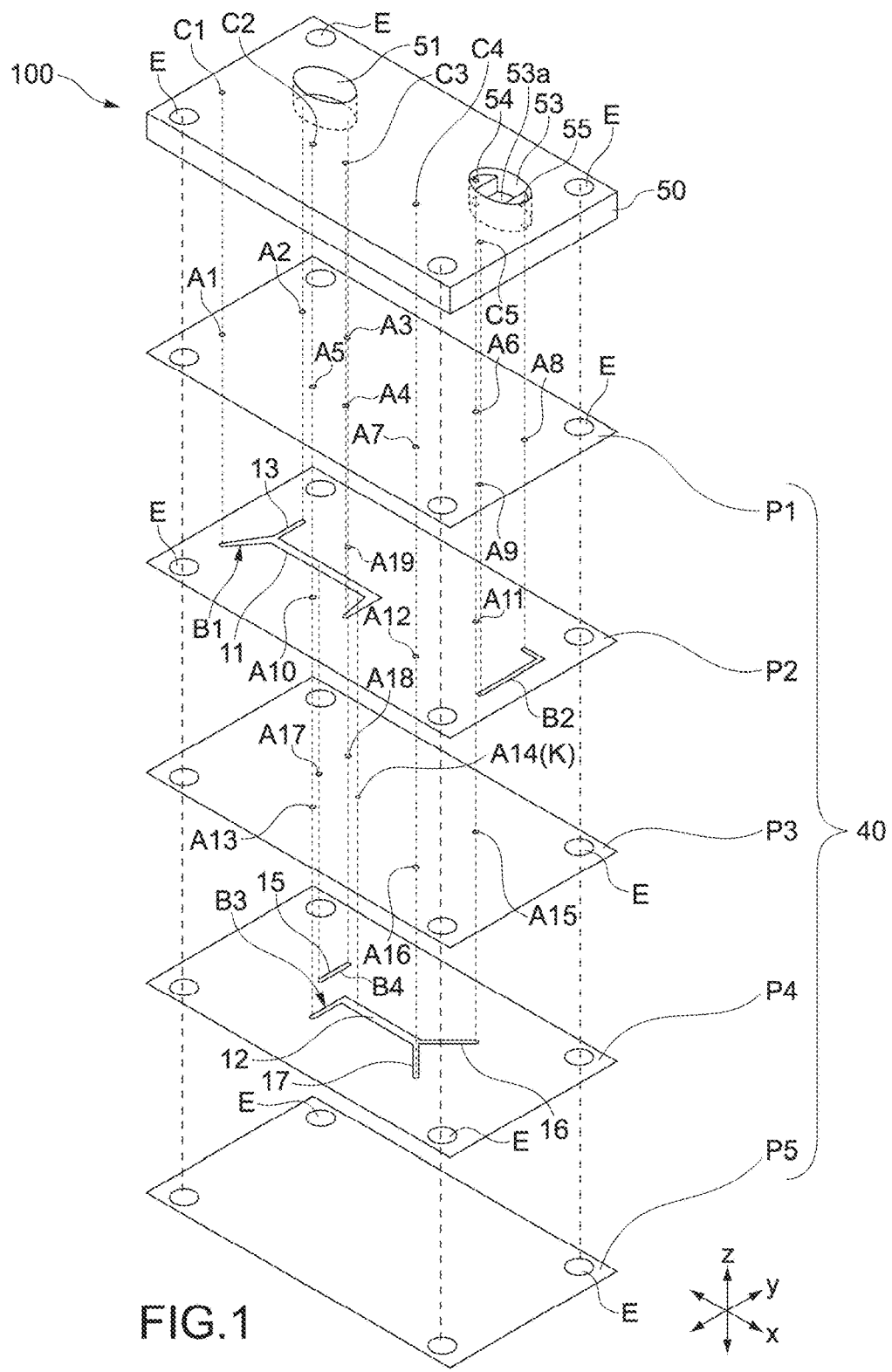
FIG. 1 is an exploded perspective view of a flow channel device according to an embodiment of the present technique.
Figure 2:
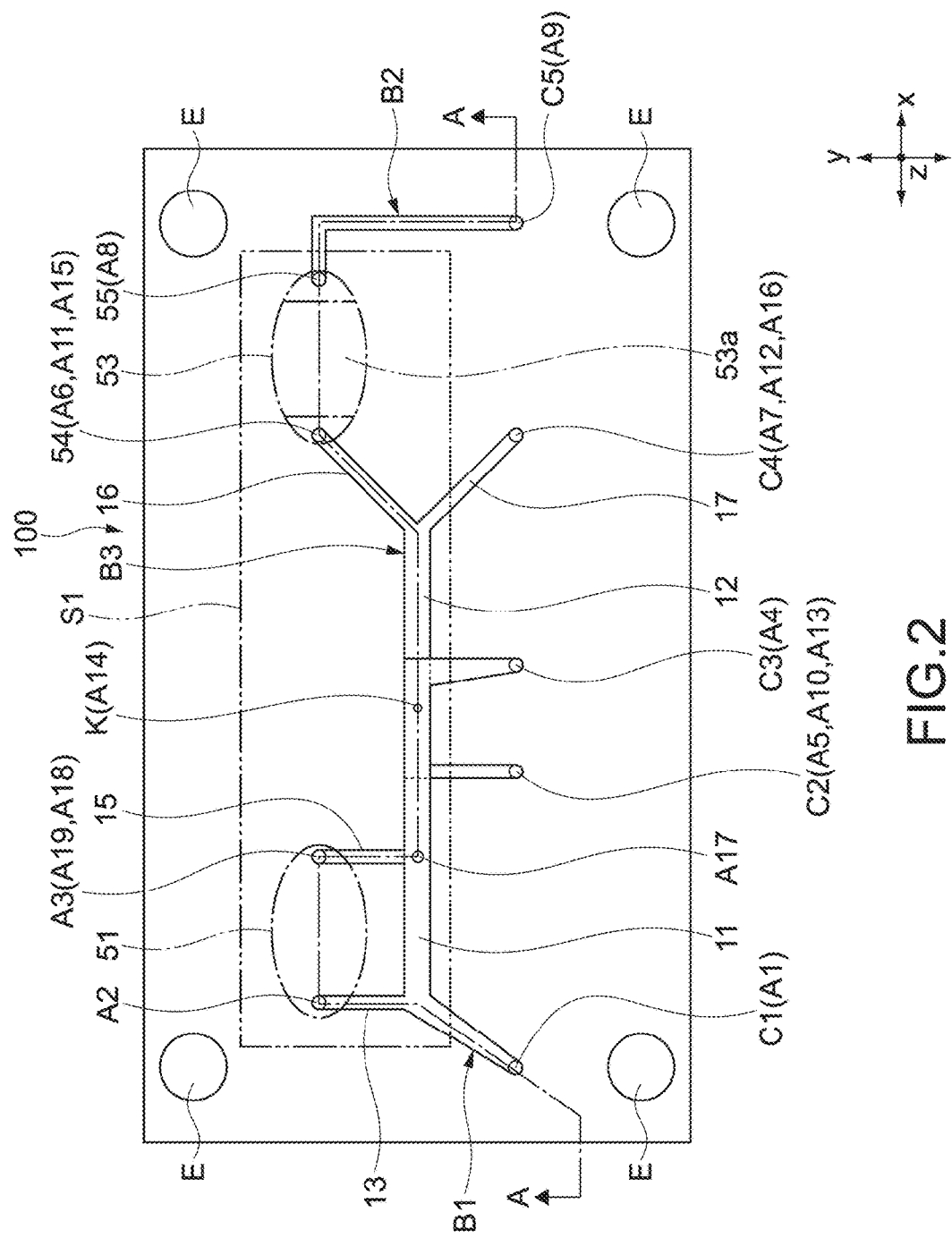
FIG. 2 is a plan view mainly showing a flow channel of the flow channel device.
Figure 3:
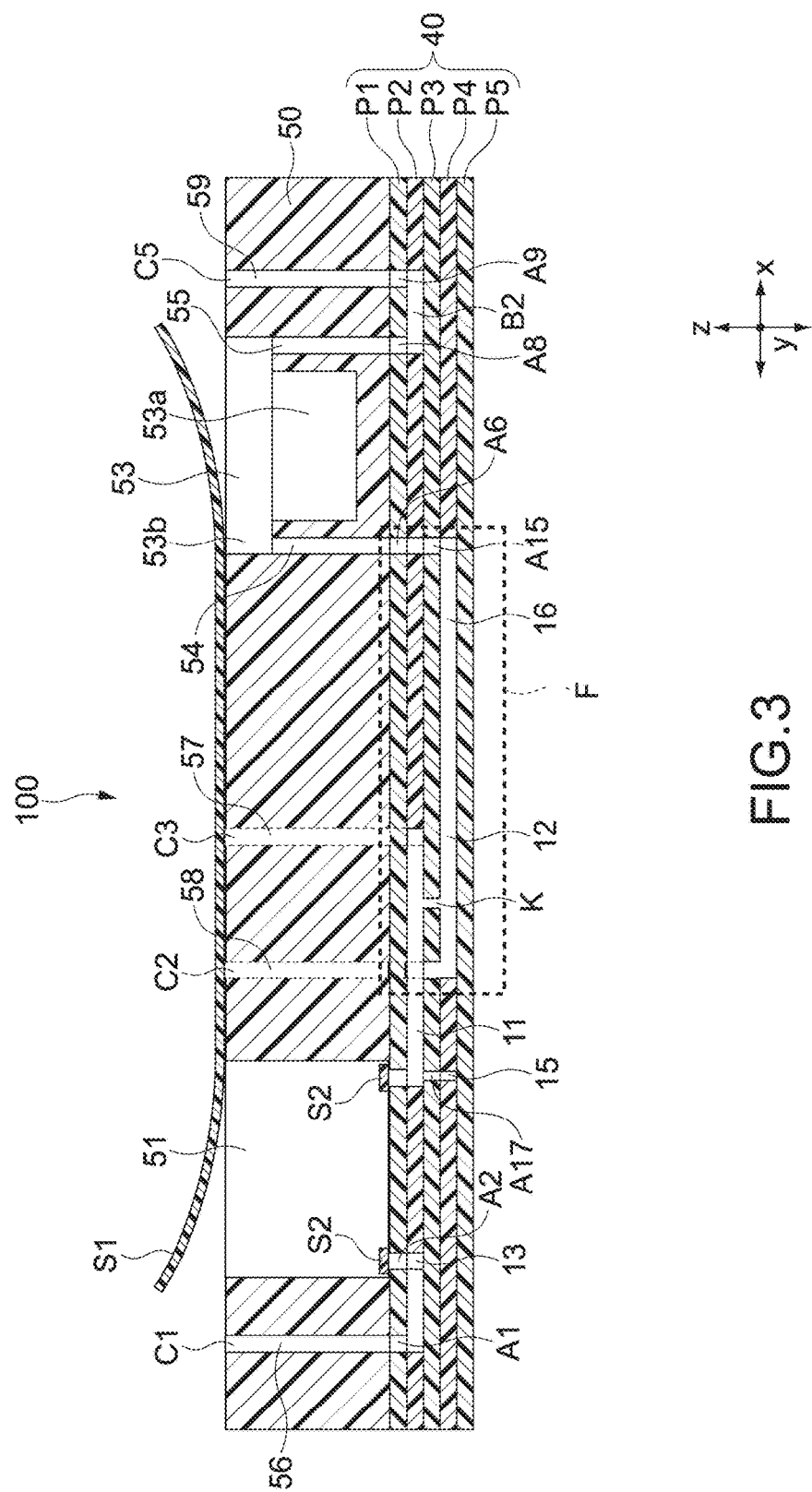
FIG. 3 is a cross-sectional diagram taken along the line A-A of FIG. 2.

FIG. 1 is an exploded perspective view of a flow channel device according to an embodiment of the present technique. FIG. 2 is a plan view mainly showing a flow channel of the flow channel device 100. FIG. 3 is a cross-sectional diagram taken along the line A-A of FIG. 2. As will be described later, particles such as biological cells are used as a sample, and the flow channel device 100 is a device that causes a fluid including those particles to flow through the flow channel.

As shown in FIG. 2, the flow channel device 100 includes a flow channel layer 40 and a vessel layer 50 provided above the flow channel layer 40. As shown in FIG. 1, the flow channel layer 40 includes a plurality of, for example, 5 films P1, P2, P3, P4, and P5 that each use a resin as its base material. Typically, the vessel layer 50 is also formed of a material that includes a resin as a base material. The films P1 to P5 have substantially the same size and outer shape. The flow channel layer 40 is formed by laminating and bonding the films P1 to P5, and the flow channel device 100 is formed by laminating and bonding the flow channel layer 40 and the vessel layer 50.

As shown in FIG. 1, on predetermined films out of the films P1 to P5, ports A1, A2, . . . as holes are formed, and channels B1, B2, . . . as slits are formed in predetermined shapes. The ports and channels penetrate the films from a front surface (upper surface) to a back surface (lower surface). Therefore, by the channels being in communication with one another via the ports and the ports being in communication with one another via the channels, a flow channel in an arbitrary shape is formed 3-dimensionally across multiple layers. It should be noted that the film P5 does not include the port and the channel and functions as a cover.

It should be noted that to help understand the drawings, the ports and channels are intentionally illustrated with large widths, but the widths are actually minute widths of about several μm to several hundred μm.

The vessel layer 50 includes an injection vessel section 51 formed by a through hole and a collection vessel section 53 formed as a concave section. The injection vessel section 51 has a structure in which a front surface of the flow channel layer 40 is a bottom thereof. A fluid including particles is injected into the injection vessel section 51. When the particles are a biological sample, a normal saline solution or the like is used as the fluid. Particles processed by the flow channel layer 40 are collected in the collection vessel section 53. Also in the vessel layer 50, ports C1, C2, . . . as holes (through holes) are formed. In the collection vessel section 53, a collection vessel inflow channel 54 and a collection vessel outflow channel 55 as holes (through holes) are provided as will be described later.

As shown in FIGS. 1 and 2, the channels B1 and B2 are formed on the film P2, and the channels B3 and B4 are formed on the film P4. Parts of the channels B1 and B3 overlap each other when seen in plan view.

The channel B1 provided in the film P2 mainly forms a first flow channel 11, an injection vessel inflow channel 13, and an injection vessel outflow channel 15. The channel B3 provided in the film P4 mainly forms a second flow channel 12 and a branch section (plurality of branch channels 16 and 17). As shown in FIG. 2, the second flow channel 12 is provided below the first flow channel 11, and the first flow channel 11 and the second flow channel 12 communicate with each other via a narrowing channel K (port A14) formed on the film P3. A flow channel cross-sectional area of the narrowing channel K is smaller than that of other flow channels of the flow channel device 100. A diameter of the narrowing channel K is set to be about a size with which a single particle can pass through (10 to 20 μm), for example.

The port C1 of the vessel layer 50 functions as an inlet of a first inflow channel 56 into which a fluid not including particles flows, and the port C1 is connected to an upstream end of the first flow channel 11 via the port A1 of the film P1. The injection vessel inflow channel 13 is branched toward an upstream side from the first flow channel 11, and the injection vessel outflow channel 15 is branched toward a downstream side from the first flow channel 11. The injection vessel outflow channel 15 is the channel B4 provided in the film P4.

A downstream end of the injection vessel inflow channel 13 is connected to the injection vessel section 51 via the port A2 of the film P1. An upstream end of the injection vessel outflow channel 15 is connected to the injection vessel section 51 via the port A18 provided in the film P3, the port A19 provided in the film P2, and the port A3 provided in the film P1. Specifically, the injection vessel inflow channel 13, the injection vessel section 51, and the injection vessel outflow channel 15 are formed so as to circumvent from the first flow channel 11. A downstream end of the first flow channel 11 is connected to a first outflow channel 57 (outflow channel) and the port C3 of the vessel layer 50 via the port A4 of the film P1, that is, in communication with an outside of the flow channel device 100.

A width of the flow channel formed along an x direction (width in y direction in FIG. 2) in the first flow channel 11 of the channel B1 is set to be larger than the widths of the injection vessel inflow channel 13, the injection vessel outflow channel 15, and the like (width in x direction in FIG. 2). The structure of the injection vessel outflow channel 15 in particular is designed as follows.

Figure 6:
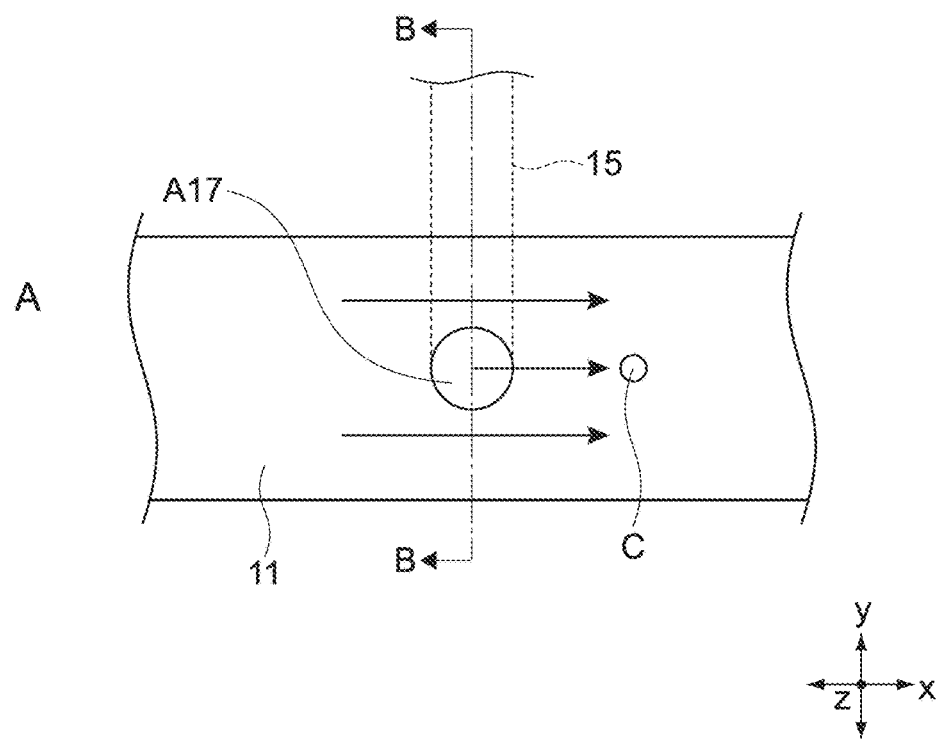
FIG. 6A is a plan view showing the vicinity of an interflow of a first flow channel and an injection vessel outflow channel.
FIG. 6B is a cross-sectional diagram taken along the line B-B of FIG. 6A.
Figure 6:
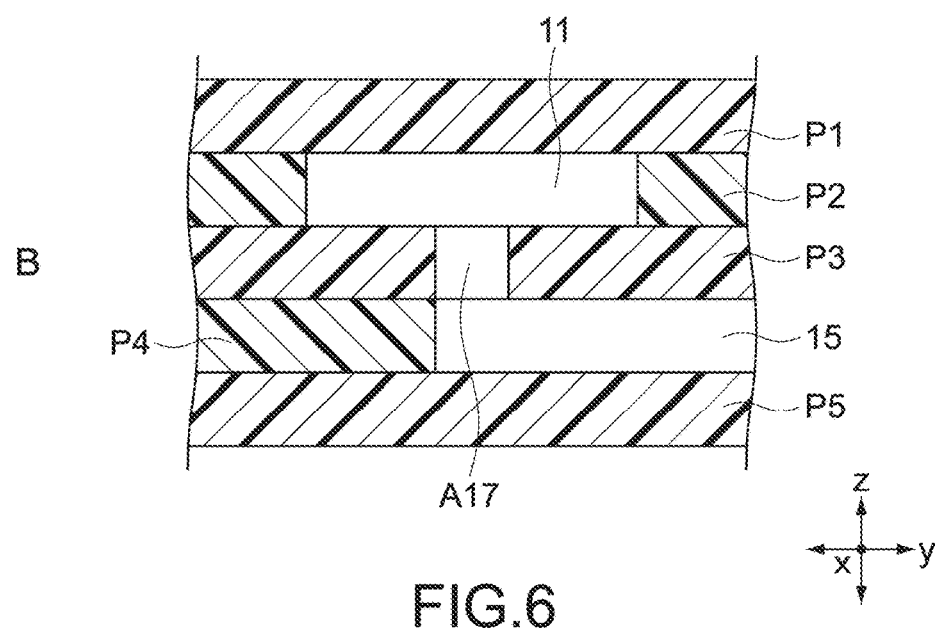

FIG. 6A is a plan view showing the vicinity of an interflow of the first flow channel 11 and the injection vessel outflow channel 15. FIG. 6B is a cross-sectional diagram taken along the line B-B of FIG. 6A. The flow channel cross-sectional area of the injection vessel outflow channel 15 is designed to be smaller than that of the first flow channel 11. Moreover, the injection vessel outflow channel 15 is connected to and joins the first flow channel 11 via the port A17 at substantially the center position of the first flow channel 11 in a direction orthogonal (y direction herein) to a flowing direction of the first flow channel 11 (x direction herein).

Specifically, flow channel resistances of the injection vessel outflow channel 15 and the first flow channel 11 are designed and a flow rate at a time a fluid flows out by a flow control mechanism 76 to be described later is set such that a flow rate ratio of the injection vessel outflow channel 15 to the first flow channel 11 falls within a range of 1:2 to 1:100. For example, the injection vessel outflow channel 15 has a flow channel width of about 2 to 10 times the diameter of the particle C, and the width of the first flow channel 11 is sufficiently larger than that. Favorably, the flow rate ratio of the injection vessel outflow channel 15 to the first flow channel 11 is 1:5 to 1:20, more favorably, 1:9. Accordingly, the particles can be aligned one by one as will be described later.

It should be noted that the flow channel cross-sectional area of the injection vessel inflow channel 13 is designed to be smaller than that of the first flow channel 11 similar to the injection vessel outflow channel 15, but the structure is not limited thereto, and the flow channel cross-sectional area may be the same as that of the first flow channel 11.

The port C2 of the vessel layer 50 functions as an inlet of a second inflow channel 58 into which a fluid not including particles flow. The port C2 is connected to the upstream end of the second flow channel 12 of the channel B3 via the ports A5, A10, and A13 of the films P1, P2, and P3, respectively. Further, a downstream end of the branch channel 16 out of the two branch channels 16 and 17 is connected to the collection vessel inflow channel 54 of the vessel layer 50 via the ports A15, A11, and A6 of the films P3, P2, and P1, respectively. A downstream end of the branch channel 17 is connected to an outflow channel of the vessel layer 50 (functions as second outflow channel) and the port C4 as an inlet thereof, that is, in communication with an outside of the flow channel device 100, via the ports A16, A12, and A7 of the films P3, P2, and P1, respectively.

The collection vessel outflow channel 55 of the vessel layer 50 is connected to the upstream end of the channel B2 of the film P2 via the port A8 of the film P1. The downstream end of the channel B2 is connected to the port C5 of the vessel layer 50 and is in communication with the outside via the port A9 of the film P1 and the outflow channel (functions as second outflow channel) 59 of the vessel layer 50.

As shown in FIG. 3, on a front surface of the vessel layer 50, a film-type seal member S1 that is formed of, for example, a resin or paper and is capable of covering the injection vessel section 51 and the collection vessel section 53 is provided. A lower surface of the seal member S1 has a viscosity, and an adhesive layer is provided in the surface, for example. It is favorable for the adhesive layer of the seal member S1 to be capable of adhering repetitively. As the seal member S1, a generally-used adhesive tape, a tack seal, or the like may be used. Since a fluid applied with a pressure flows through the flow channel as will be described later, a fluid pressure can be generated in the flow channel due to the injection vessel section 51 and the collection vessel section 53 being sealed by the seal member S1.

By providing the film-type seal member S1 having a flexibility as described above, there is an advantage that it is easy to remove air bubbles remaining in the injection vessel section 51 as will be described later.

A seal member formed of rubber or the like, that is detachable with respect to the vessel layer 50, for example, may be provided in the front surface of the vessel layer 50 in place of the film-type seal member S1 having a viscosity as described above. However, manufacture costs can be cut and the flow channel device 100 becomes a device suited for a disposable use with the film-type seal member S1 as compared to the seal member formed of rubber or the like.

Figure 4:
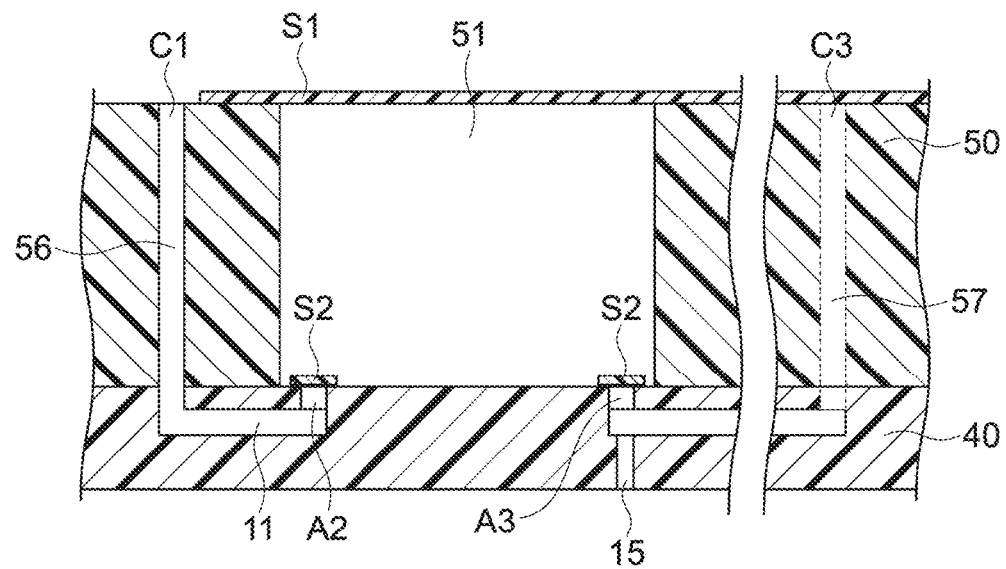
FIG. 4 is a cross-sectional diagram showing the vicinity of an injection vessel section of a vessel layer.

FIG. 4 is a cross-sectional diagram showing the vicinity of the injection vessel section 51 of the vessel layer 50. FIG. 4 shows the vessel layer 50 and partial layers (films P1 to P4) of the flow channel layer 40.

The flow channel device 100 includes valves S2 between the injection vessel section 51 and the flow channel of the flow channel layer 40. For example, the valves S2 are attached to the bottom of the injection vessel section 51 between the ports A2 and A3 and the injection vessel section 51 and are each a water-soluble seal, for example. As a material of the water-soluble seal, there are, for example, a pharmaceutical film and a water-soluble film used as a food film in addition to a starch and pullulan.

The ports A2 and A3 and the flow channels connected to the injection vessel section 51, such as the injection vessel inflow channel 13 and the injection vessel outflow channel 15, may have a hydrophobic property in place of the water-soluble seal. With this structure, depending on the type of fluid or sample, the injection vessel section 51 can store the fluid including the particles inside even without a seal. In this case, it is favorable to set the widths of the flow channels 13 and 15 to be about several ten μm or the like. Such a hydrophobic flow channel structure is also applicable to the collection vessel section 53.

Figure 5:
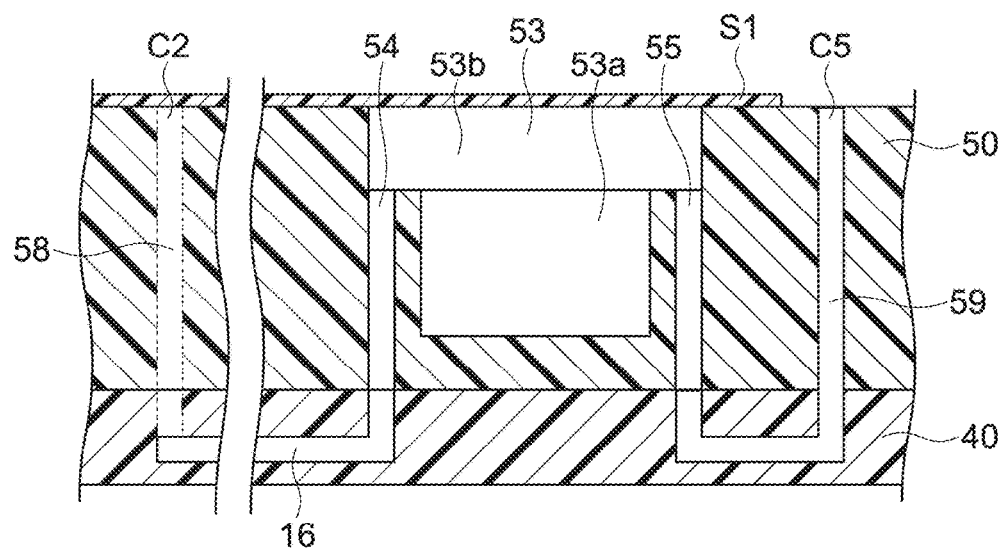
FIG. 5 is a cross-sectional diagram showing the vicinity of a collection vessel section of the vessel layer.

FIG. 5 is a cross-sectional diagram showing the collection vessel section 53 of the vessel layer 50. FIG. 5 also shows the vessel layer 50 and the partial layers (films P1 to P4) of the flow channel layer 40 as in FIG. 4.

As shown in FIGS. 1, 3, and 5, a concave accumulation section 53a capable of accumulating mainly a sample is provided inside the collection vessel section 53. The accumulation section 53a has a predetermined depth from the front surface of the vessel layer 50. In the collection vessel section 53, an area 53b shallower than the accumulation section 53a is provided in an outer side of the accumulation section 53a. The collection vessel inflow channel 54 is connected to the front surface of the shallow area 53b, and the collection vessel outflow channel 55 is connected to the front surface of the shallow area 53b at a position opposing the collection vessel inflow channel 54.

Figure 7:
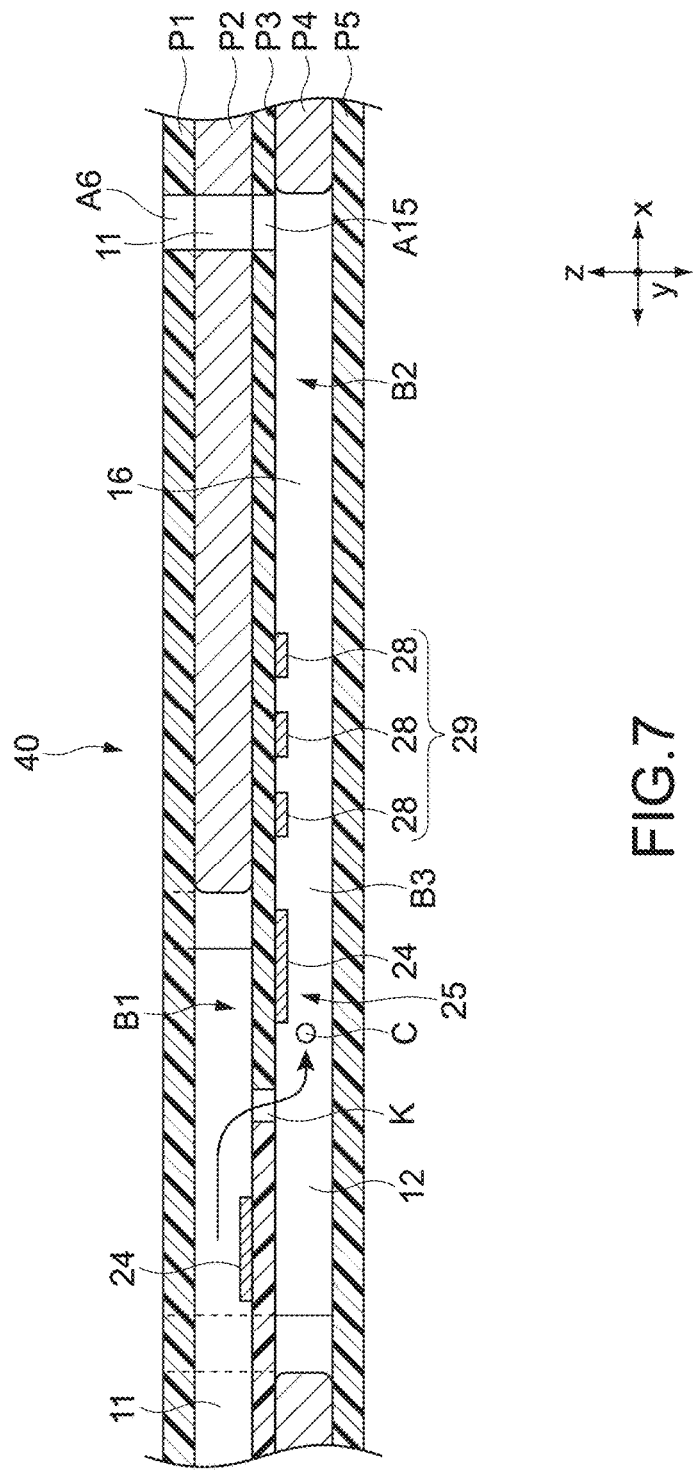
FIG. 7 is a partially-enlarged diagram showing a square area surrounded by a broken line in FIG. 3.

FIG. 7 is an enlarged diagram showing a square part F surrounded by a broken line in FIG. 3. The flow channel device 100 of this embodiment is a device that sorts particles, such as a cell sorter. The flow channel device 100 includes a measurement electrode section 25 as a conductive section, and the measurement electrode section 25 includes electrodes 24 (electrode pair) constituting a parallel plate-type capacitor. The electrodes 24 are arranged so as to sandwich the narrowing channel K. Specifically, the electrodes 24 are respectively arranged on a bottom surface of the first flow channel 11 and a ceiling surface of the second flow channel 12. For example, an AC measurement voltage signal is applied onto the measurement electrode section 25, and an electrical amount of the fluid including the particles C in the narrowing channel K at the time the particles C pass through the narrowing channel K is measured.

In the second flow channel 12, an operation electrode section 29 constituted of a plurality of electrodes 28 is provided in a downstream side of a position where the electrodes 24 are provided and on an upstream side of the branch channels (branch channels 16 and 17). The electrodes 28 are arranged along the x direction as a main flowing direction in the second flow channel 12. By applying an operation voltage signal onto the operation electrode section 29, an electrophoretic force or a dielectrophoretic force can be imparted to the particles C. The electrophoretic force causes a displacement of a path of the particles C, and one of the branch channels 16 and B3b is selected as the path of the particles C.

The base material of the films P1 to P5 of the flow channel layer 40 is typically polyimide. In the flow channel layer 40 shown in FIG. 1, the first, third, and fifth films P1, P3, and P5 from the top are non-thermoplastic polyimide films, and the second and fourth films P2 and P4 from the top are thermoplastic polyimide films, for example. In other words, the non-thermoplastic polyimide films P1, P3, and P5 and the thermoplastic polyimide films P2 and P4 are laminated alternately and bonded. Since the films P1 to P5 are formed of polyimide, the adhesiveness of the films can be enhanced.

For the material as the base material of the films P1 to P5, PDMS (polydimethylsiloxane or dimethylpolysiloxane), acryl, PES (polyether sulfone), polycarbonate, polypropylene, polystyrene, polyimide, COP (cyclic olefin polymer), COC (cyclic olefin copolymer), or the like is used in place of polyimide.

Polyimide is also typically used for the material as the base material of the vessel layer 50, but other known resin materials as described above may also be used. When polyimide is used as the material of the vessel layer 50, thermoplastic polyimide is typically used, though non-thermoplastic polyimide may be used instead. The material of the vessel layer 50 and the material of the flow channel layer 40 may differ.

The thickness of the films P1 to P5 is, for example, 5 to 300 μm, more favorably, 10 to 100 μm, 20 to 80 μm, 40 to 60 μm, or 50 μm. The thickness of the films P1, P3, and P5 that include non-thermoplastic polyimide as the base material may differ from that of the films P2 and P4 that include thermoplastic polyimide as the base material. In this embodiment, the films P2 and P4 that include thermoplastic polyimide as the base material are thicker than the films P1, P3, and P5 that include non-thermoplastic polyimide as the base material. All the films P1 to P5 may of course have the same thickness.

The thickness of the vessel layer 50 is larger than that of the flow channel layer 40 and is, for example, 1 mm or more and a few cm or less.

The channels, ports, and conductive sections are formed on the base materials of the films P1 to P5 typically by a technique of a photolithography, etching, or the like. The vessel layer 50 is formed by, for example, injection molding or heat press molding.

After the channels, ports, and conductive sections are formed, fixture pins (not shown) are inserted into positioning holes E commonly formed at 4 corners of each of the films P1 to P5 and the vessel layer 50. Then, after being positioned and laminated, the films P1 to P5 and the vessel layer 50 are bonded by processing of pressure bonding (e.g., thermal compression bonding) or the like.

It should be noted that the holes E may be formed by the photolithography and etching processing described above or may be formed by other mechanical processes.

The bonding process of the films P1 to P5 and the bonding process of the vessel layer 50 with respect to the films P1 to P5 may be carried out as different processes. In other words, the vessel layer 50 may be bonded to the flow channel layer 40 after the flow channel layer 40 is formed.

When the films P1 to P5 are formed of polyimide, a heating temperature for the pressure bonding is set to a temperature near a glass transition point (about 250°) of polyimide, which is 250° C.±50° C., for example. By the heating, the thermoplastic polyimide films P2 and P4 are softened and expanded to thus be bonded to the non-thermoplastic polyimide films P1, P3, and P5. Accordingly, the flow channel layer 40 is formed.

When the films P2 and P4 are thermoplastic polyimide films, the films P1 to P5 are bonded by remelting of the thermoplastic material itself. Therefore, there is no need to use an adhesive. Further, since all the films P1 to P5 are formed of the same material such as polyimide, the adhesiveness of the films can be enhanced as described above.

By using the same material such as polyimide as the base material of the flow channel layer 40 and the vessel layer 50, the flow channel layer 40 and the vessel layer 50 can be bonded without using an adhesive.

The films P1 to P5 of the flow channel layer 40 may of course be adhered onto one another by an adhesive. The same holds true for the adhesion of the flow channel layer 40 and the vessel layer 50. For example, an adhesive layer may be formed in advance (before bonding process) on the front surface of the vessel layer 50 and/or the flow channel layer 40. While an epoxy resin having a thermosetting property is used as the material of the adhesive, for example, resins having a thermoplasticity, a photo (e.g., ultraviolet rays)-curability, and the like may be used instead.

The conductive sections constituting the electrode sections 25 and 29 shown in FIG. 7 may be formed of, for example, copper, silver, gold, platinum, nickel, zinc, titanium, or stainless steel, or may be formed by performing various types of plating processing on those sections.

2. Analysis Apparatus

Figure 8:
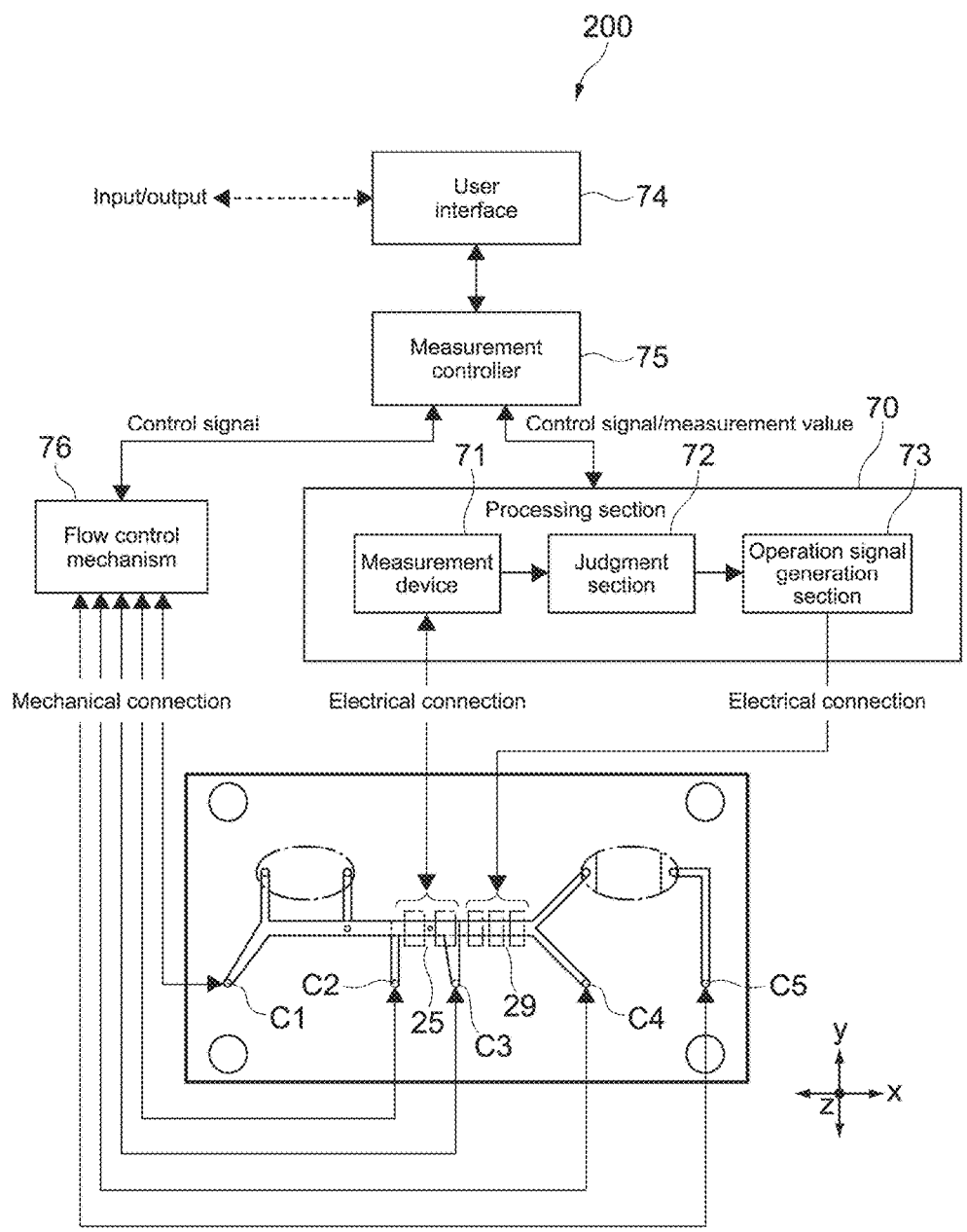
FIG. 8 is a block diagram showing a structure of an analysis apparatus including the flow channel device.

FIG. 8 is a block diagram showing a structure of an analysis apparatus including the flow channel device 100.

The analysis apparatus 200 mainly includes the flow channel device 100, a measurement controller 75, a processing section (device) 70 electrically connected to the flow channel device 100, and a flow control mechanism 76 that controls the fluid of the flow channel device 100.

The user is capable of inputting information to the measurement controller 75 using a user interface 74 constituted of a keyboard, a mouse, a touch panel, and the like. The measurement controller 75 outputs a control signal corresponding to input information to the processing section 70 and acquires a measurement value of an electrical amount or the like to be described later measured by the processing section 70 or other data. The measurement controller 75 is also capable of outputting the information output from the processing section 70 and the flow control mechanism 76 to a higher-order device to put it in a user presentable state.

The measurement controller 75 and the processing section 70 are mainly constituted of a computer such as a PC and a dedicated device. The measurement controller 75 and the processing section 70 may be physically-separate apparatuses or may be integrated.

The flow channel device 100 is mainly mechanically connected to the flow control mechanism 76 that controls a flow of the fluid in the flow channel device 100. The flow control mechanism 76 includes a pump, a pressure tank, a flowmeter, and a pressure meter. For example, the flow control mechanism 76 is connected to the ports C1 to C5 of the flow channel device 100 via a tube, valve, and the like. A fluid apparatus is constituted of at least the flow channel device 100 and the flow control mechanism 76.

The processing section 70 includes a measurement device 71, a judgment section 72, and an operation signal generation section 73 and is electrically connected to the measurement electrode section 25 and the operation electrode section 29 of the flow channel device 100, for example. The processing section 70 generates an operation signal based on a measurement signal obtained by the measurement electrode section 25 and outputs an operation voltage corresponding to the operation signal to the operation electrode section 29.

The measurement device 71 is electrically connected to the measurement electrode section 25 of the flow channel device 100. By generating an AC measurement voltage signal of a predetermined frequency range, the measurement device 71 applies a voltage to the measurement electrode section 25 as described above. Moreover, while applying the measurement voltage signal to the measurement electrode section 25, the measurement device 71 measures an electrical amount obtained when the particles pass through the narrowing channel K. For example, since a resistance value between the electrodes 24 changes when the particles pass through the narrowing channel K, the measurement device 71 can detect a current flowing between the electrodes 24. The electrical amount is not limited to the current, and a voltage, a resistivity, an impedance, a conductivity, a conductance, a complex numerical value of those described above, and the like may also be used.

The measurement device 71 also calculates a complex impedance from the current value measured as described above. Specifically, the measurement device 71 calculates, with respect to each cell flowing through the narrowing channel K, a complex permittivity as electrical characteristics that depends on the cells across multipoint frequencies (3 or more, typically about 10 to 20 points) in an AC voltage frequency range (e.g., 0.1 MHz to 50 MHz) where a dielectric relaxation phenomenon occurs.

The measurement device 71 generates measurement data from the obtained electrical amount. For example, the measurement device 71 calculates a complex permittivity from a complex impedance using a known electrical conversion expression and obtains data including the complex permittivity as the measurement data.

As an amount electrically equivalent to the complex permittivity, there are a complex impedance, a complex admittance, a complex capacitance, a complex conductance, and the like, which are mutually convertible by the simple known electrical amount conversion described above. Further, the measurement of a complex impedance or complex permittivity includes a measurement of only a real number part or an imaginary number part.

The judgment section 72 acquires the measurement data measured by the measurement device 71 and judges whether the particle is to be sorted, that is, whether the particle is to be guided to a predetermined one (branch channel 16 in this embodiment) of the two branch channels 16 and 17, based on the measurement data. For example, the judgment section 72 collates the measurement data with a judgment condition of data arbitrarily preset in a memory for sorting desired particles to carry out judgment processing.

The operation signal generation section 73 generates an operation signal when the measurement target particle is a particle to be sorted (particle to be guided to the branch channel 16 in this case) and does not generate an operation signal otherwise. Alternatively, it is also possible for the operation signal generation section 73 to not generate an operation signal when the measurement target particle is a particle to be sorted and generate an operation signal otherwise.

3. Operations of Flow Channel Device and Analysis Apparatus

Figure 9:
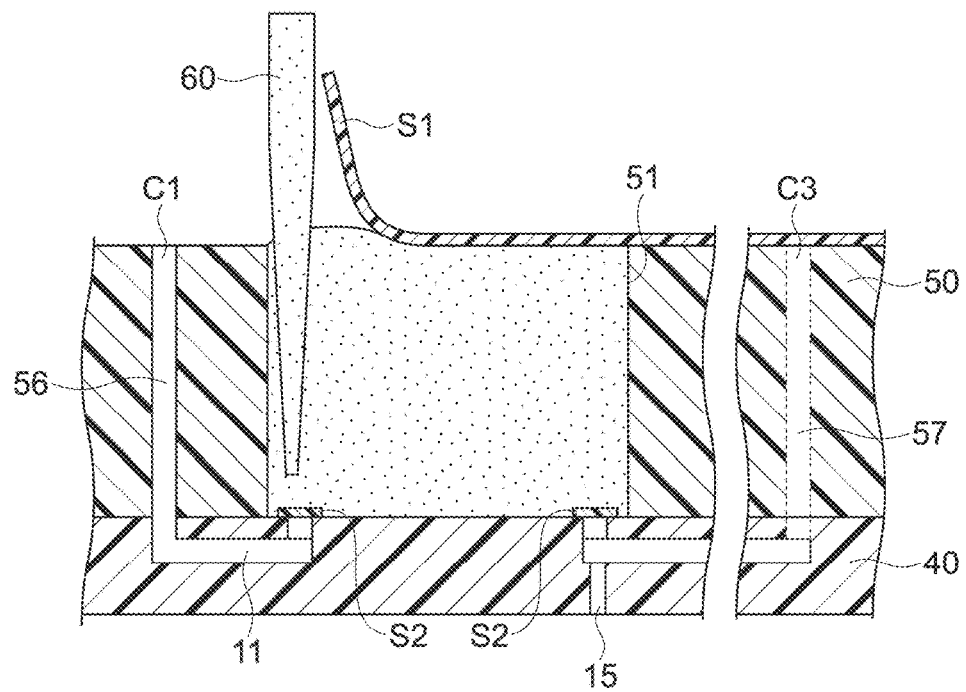
FIG. 9 shows a sample injection operation with respect to the injection vessel section.

As shown in FIG. 9, an operator removes the seal member S1 on the injection vessel section 51 to open the injection vessel section 51 and injects a fluid including particles into the injection vessel section 51 using a tool such as a pipette 60. Then, the operator reattaches the seal member S1 onto the injection vessel section 51 to seal the injection vessel section 51. In this case, when pneumatically causing the fluid to flow in the flow channel device 100, it is favorable for air bubbles to not remain inside the injection vessel section 51 to make a pressure loss as small as possible. Therefore, it is favorable to inject a fluid including particles in a larger volume than the injection vessel section 51.

Here, in this embodiment, since the film-type flexible seal member S1 is provided, the operator can attach the seal member S1 while letting air bubbles out of the injection vessel section 51, that is, while gradually releasing bending of the seal member S1. Accordingly, air bubbles can be easily removed.

Figure 11:
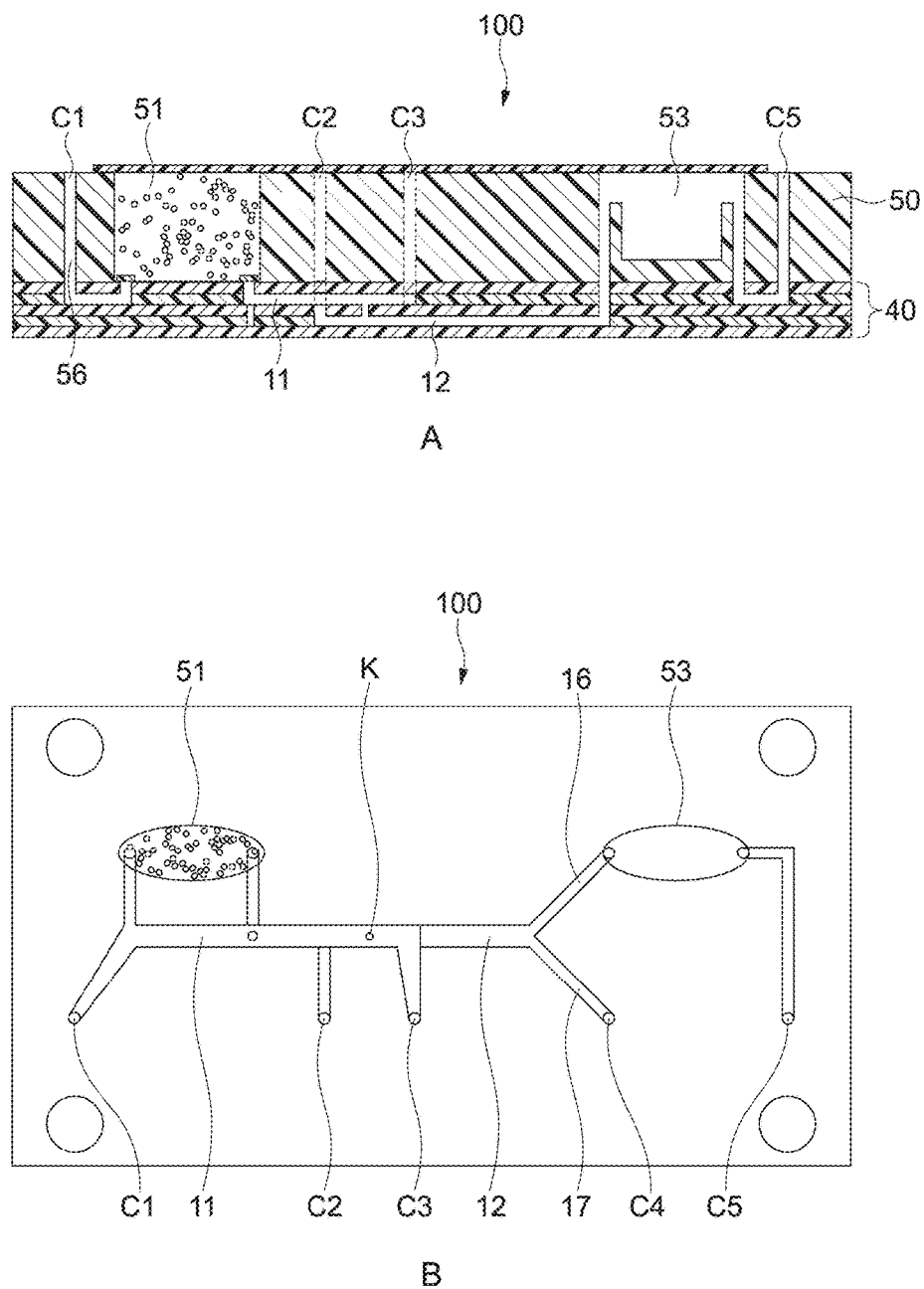
FIGS. 11A and 11B show a state where a fluid including samples is accommodated in the injection vessel section.

The valves S2 as water-soluble seals do not dissolve for a predetermined time, for example, several minutes, after the fluid is injected into the injection vessel section 51. Therefore, the injection vessel section 51 can accommodate the fluid for a predetermined time. FIGS. 11A and 11B show a state where a fluid including samples is accommodated in the injection vessel section 51.

Figure 12:
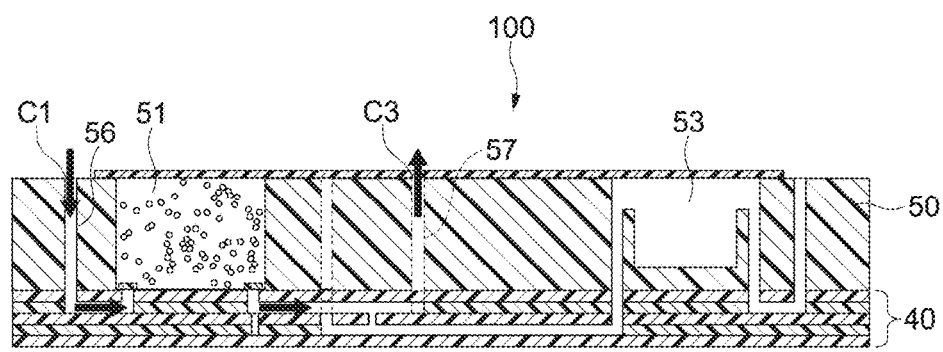
FIGS. 12A and 12B show a state where an outflow of the fluid to the first flow channel is started at the time the water-soluble seal is dissolved.
Figure 12:
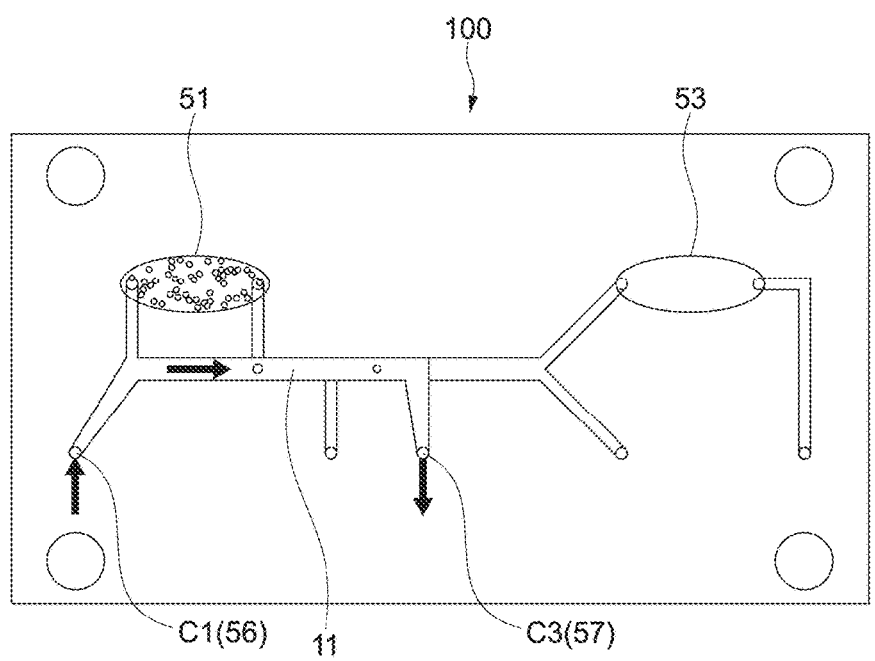

As shown in FIGS. 12A and 12B, at a timing at which the valves S2 dissolve or before the valves S2 dissolve, the flow control mechanism 76 (see FIG. 8) starts delivering a fluid into the first flow channel 11 via the port C1 and the first inflow channel 56. The fluid delivered from the flow control mechanism 76 is a fluid not including particles. The fluid is the same as the fluid including particles, that is accommodated in the injection vessel section 51, or is a fluid that does not affect the particles even when both fluids are mixed. The flow of the fluid in the first flow channel 11 is indicated by bold black arrows. While the valves S2 are not dissolved, the fluid flows through the first flow channel 11 without circumventing to the injection vessel section 51 and is discharged from the port C3 via the first outflow channel 57 as a flow channel having a larger flow channel resistance than the narrowing channel K as shown in FIGS. 12 and B.

Figure 10:
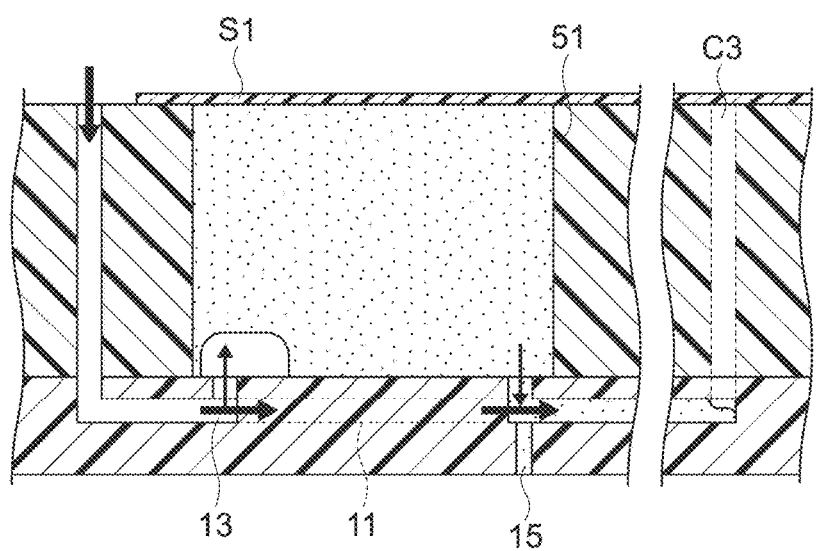
FIG. 10 shows a fluid flow in the vicinity of the injection vessel section when a water-soluble seal is dissolved.

After the valves S2 dissolve, the fluid that has flown through the first flow channel 11 until then is branched to the injection vessel inflow channel 13 and flows into the injection vessel section 51 as shown in FIG. 10. By the fluid pressure, the fluid including particles in the injection vessel section 51 flows out to the injection vessel outflow channel 15 and joins the first flow channel 11. As described above, based on a relationship of the flow channel resistances of the injection vessel outflow channel 15 and the first flow channel 11, the fluid that has flown out of the injection vessel outflow channel 15 joins the fluid flowing through the first flow channel 11 (see FIGS. 6A and 6B) to form a laminar flow in the first flow channel 11. Accordingly, the particles can flow through the first flow channel 11 in an aligned state.

In this embodiment, by providing the valves S2, the fluid can be caused to flow without a valve for mechanically opening and closing the vessel section.

The valve leading to the port C3 is opened by the flow control mechanism 76 until the particles stably flow through the first flow channel 11, and the fluid including the particles is discharged via the first outflow channel and the port C3. A time required for the particles to stably flow through the first flow channel 11 after the valves S2 dissolve and the particles flow out of the injection vessel section 51 is about several seconds.

For checking whether the particles are stably flowing, the inside of the first flow channel 11 may be captured by a camera or the like from above the flow channel device 100 so that a judgment can be made by an analysis of the image by a computer or a visual check of the image by a human being.

When the particles are stably flowing through the first flow channel 11, the valve leading to the port C3 is closed by the flow control mechanism 76, and the discharge of the fluid from the first outflow channel is restricted (see FIGS. 13A and 13B). Accordingly, the fluid including the particles, that is flowing through the first flow channel 11, flows into the second flow channel 12 via the narrowing channel K.

As shown in FIGS. 13A and 13B, at a timing at which or after the discharge of the fluid from the first outflow channel is restricted, the flow control mechanism 76 opens the valve leading to the port C4 to cause a fluid not including the particles to flow into the second flow channel 12 from the port C2 via the second inflow channel 58. At this time, a valve leading to the port C5 is closed, but the flow control mechanism 76 may also open the valve leading to the port C5 at a timing of opening the port C4 or right after opening the port C4 (see FIGS. 14A and 14B).

Figure 13:
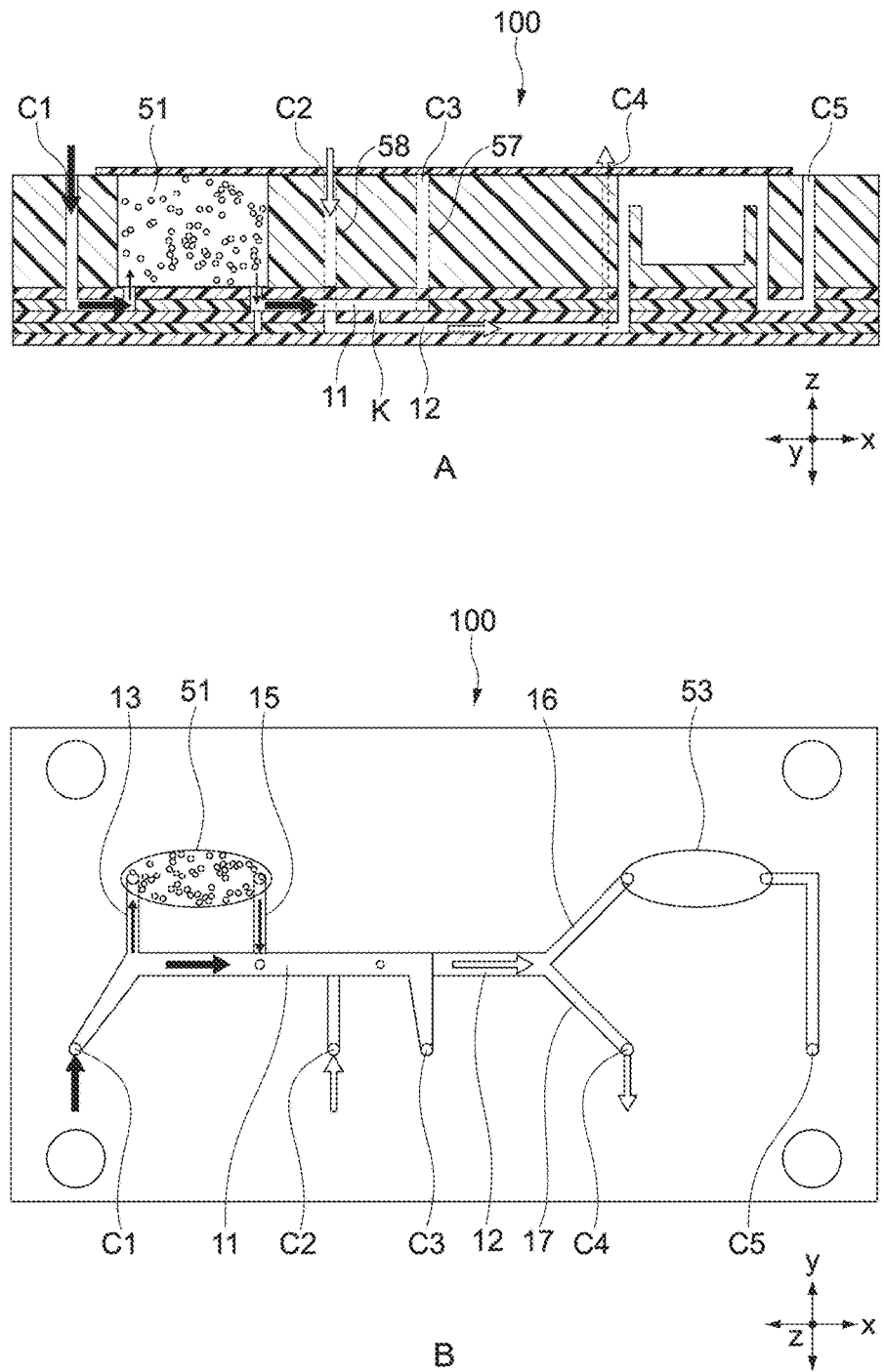
FIGS. 13A and 13B show a state where a discharge of the fluid from the first outflow channel is restricted and an outflow of the fluid to the second flow channel is started.
Figure 14:
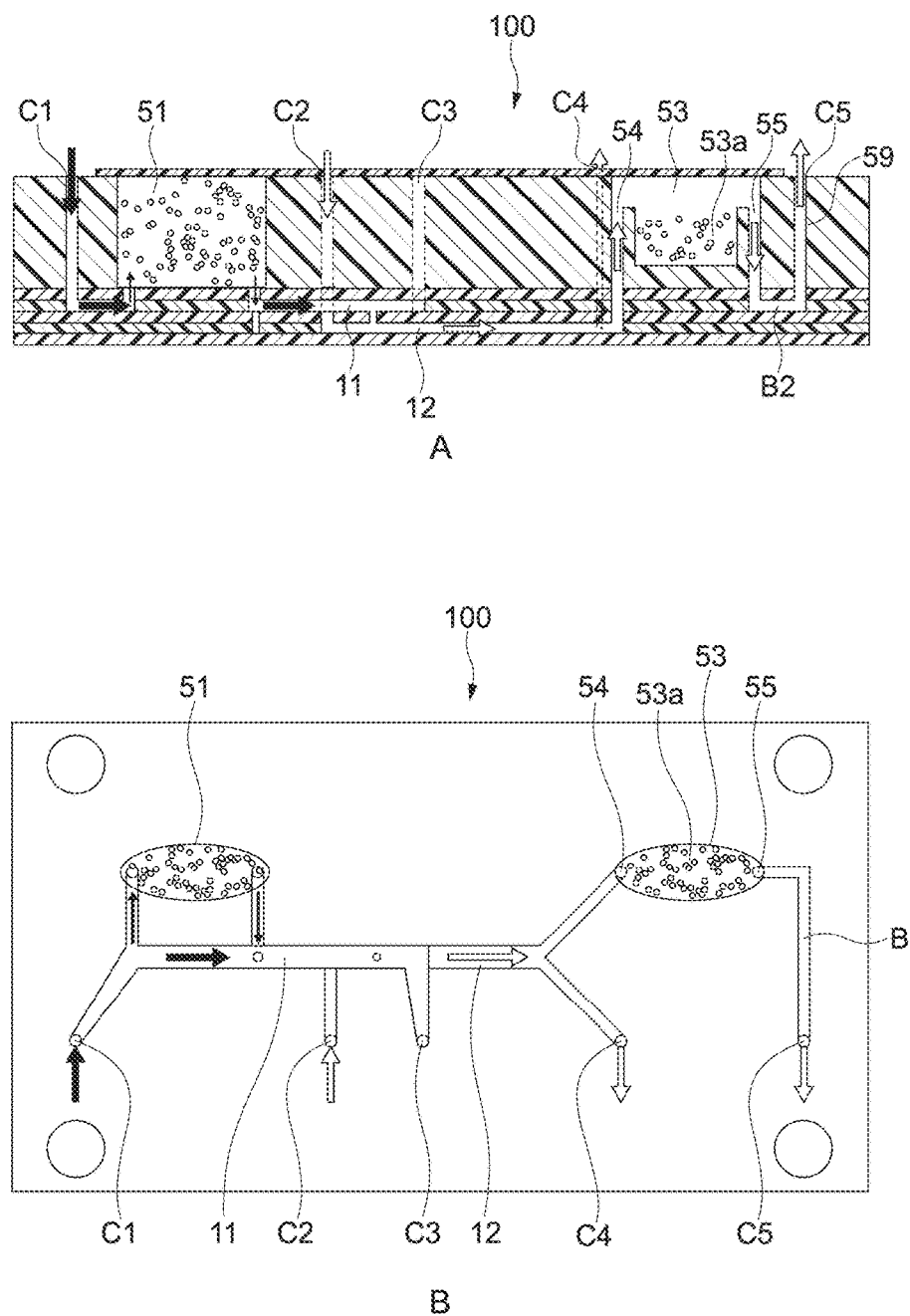
FIGS. 14A and 14B show a state where a discharge of the fluid from the second outflow channel is started.
Figure 15:
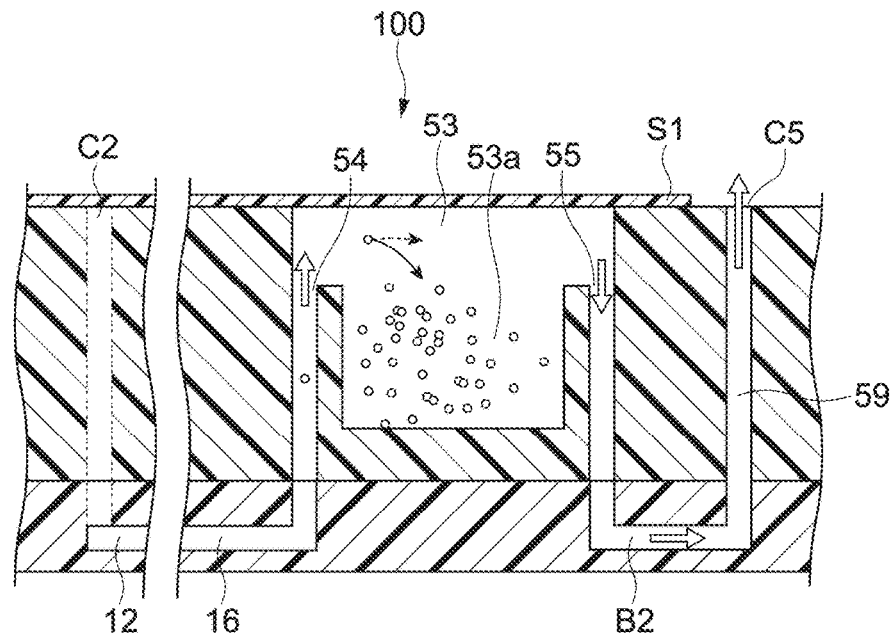
FIG. 15 shows a state where particles are accommodated in an accommodation section of the collection vessel section.

The fluid flowing through the second flow channel 12 is indicated by bold white arrows in FIG. 13 and subsequent figures. The fluid joins the fluid flowing through the first flow channel 11 on the downstream side of the narrowing channel K. Specifically, a fluid flow in the second flow channel 12 (crossflow) including a velocity component (velocity component in horizontal direction; x component herein) orthogonal to the flowing direction of the fluid including the particles (z direction) in the narrowing channel K is formed. Accordingly, the flowing state in the second flow channel 12 and subsequent channels is dominated by the crossflow, and the flow of the particles in the second flow channel 12 can be stabilized. As a result, the particles that have exited the narrowing channel K readily moves away from the narrowing channel K to flow through the second flow channel 12. Therefore, it is possible to prevent the particles from returning to the periphery of the narrowing channel K.

The flow rate ratio of the first flow channel 11 to the second flow channel 12 is set within the range of, for example, 1:5 to 1:1000.

When the particles pass through the narrowing channel K, the processing section 70 (see FIG. 8) measures the electrical amount of the fluid including the particles in the narrowing channel K using the measurement voltage signal of the measurement electrode section 25 and specifies a type and state of the particles as described above. Here, since a crossflow is formed as described above, the flow of the particles is stabilized, and a measurement accuracy of each of the particles in the measurement electrode section 25 can be enhanced.

The processing section 70 judges whether to generate and output an operation voltage signal according to the specified type and state of the particles. When the judgment section 72 judges that the specified particle is a particle to be accumulated in the collection vessel section 53, the operation signal generation section 73 generates an operation voltage signal and applies it onto the operation electrode section 29 (see FIGS. 7 and 8). Consequently, in an area where the operation electrode section 29 is provided in the second flow channel 12, an electrophoretic force is applied to the particle so as to impart a force of a component in the y direction, and the particle is thus guided to the branch channel 16. When the judgment section 72 judges that the specified particle is not a particle to be accumulated in the collection vessel section 53, an operation voltage signal is not generated, and the particle is guided to the branch channel 17.

Of course, the structure of the second flow channel 12, the structure of the operation electrode section 29, and the like may be designed such that, when it is judged that the particle is not a particle to be accumulated in the collection vessel section 53, an operation voltage signal is generated and output so that the particle is guided to the branch channel 17.

The applicant specifically discloses the operation content of the processing section 70 and the flow channel device 100 as described above in Japanese Patent Application Laid-open No. 2012-98075 or other applications filed in the past. The disclosed contents of those specifications are within the range of the disclosure of the present technique.

It is desirable to stabilize the flow rate ratio of the two branch channels 16 and 17. For example, a pressure tank as a part of the flow control mechanism 76 is connected to each of the ports C4 and C5. The flow control mechanism 76 controls a pressure ratio between the pressure tanks to enhance the stability of the flow rate ratio of the branch channels 16 and 17.

As described above, the particle guided to the branch channel 16 is discharged outside the flow channel device 100 via the port C4. It should be noted that FIG. 13 show a cross section of the collection vessel section 53, and the branch channel 17 and the outflow channel leading to the port C4 (second outflow channel) are not illustrated. Actually, the branch channels 16 and 17 overlap each other and the second outflow channel and the collection vessel inflow channel 54 overlap each other in FIG. 13. Therefore, to help understand FIGS. 13 and 14, the outflow path of the fluid from the second outflow channel is indicated by white arrows in broken lines while being displaced from the collection vessel inflow channel 54.

As shown in FIGS. 14A and 14B, the particle guided to the branch channel 16 flows into the collection vessel section 53 via the collection vessel inflow channel 54. Inside the collection vessel section 53, an area on an outer side of the accumulation section 53a as an outlet of the collection vessel inflow channel 54 is shallower than the accumulation section 53a. It is desirable for the flow channel cross-sectional area immediately after the outlet of the collection vessel inflow channel 54 to be about tens of times the flow channel cross-sectional area of the outlet of the collection vessel inflow channel 54. Accordingly, a gravity-direction component of the velocity component of the particle that has flown out of the collection vessel inflow channel 54 becomes large as compared to that of the flowing direction of the fluid flowing toward the collection vessel outflow channel 55, that is, the velocity in the x direction is sufficiently lowered, with the result that the particle sinks toward the accumulation section 53a. The particles can thus be efficiently accumulated in the accumulation section 53a.

Moreover, since the collection vessel outflow channel 55 is arranged at a position opposing the collection vessel inflow channel 54, the fluid that has flowed into the collection vessel section 53 from the collection vessel inflow channel 54 is apt to move toward the collection vessel outflow channel 55. Therefore, the fluid can smoothly flow out of the collection vessel outflow channel 55.

Figure 16:
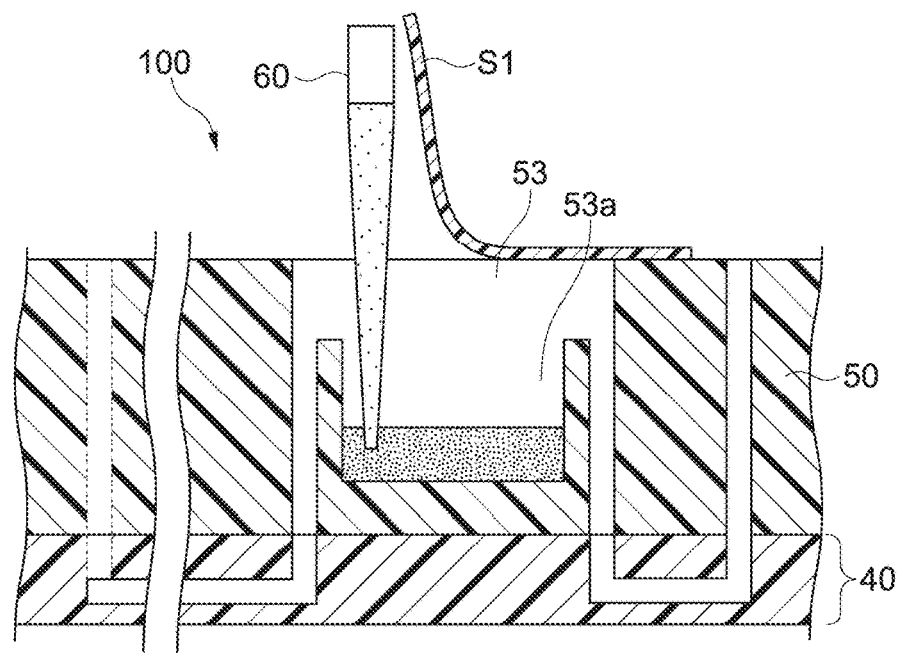
FIG. 16 shows an operation of collecting samples from the collection vessel section.

When the particles are accumulated in the accumulation section 53a and the particle sorting operation by the processing section 70 is ended, the operation of the flow control mechanism 76 is stopped, and the fluid flow in the flow channel device 100 stops. As shown in FIG. 16, the operator can peel off the seal member S1 from the vessel layer 50 to take out the fluid including the particles in a high concentration, that is accumulated in the accumulation section 53a of the collection vessel section 53 using a tool such as the pipette 60.

Figure 17:
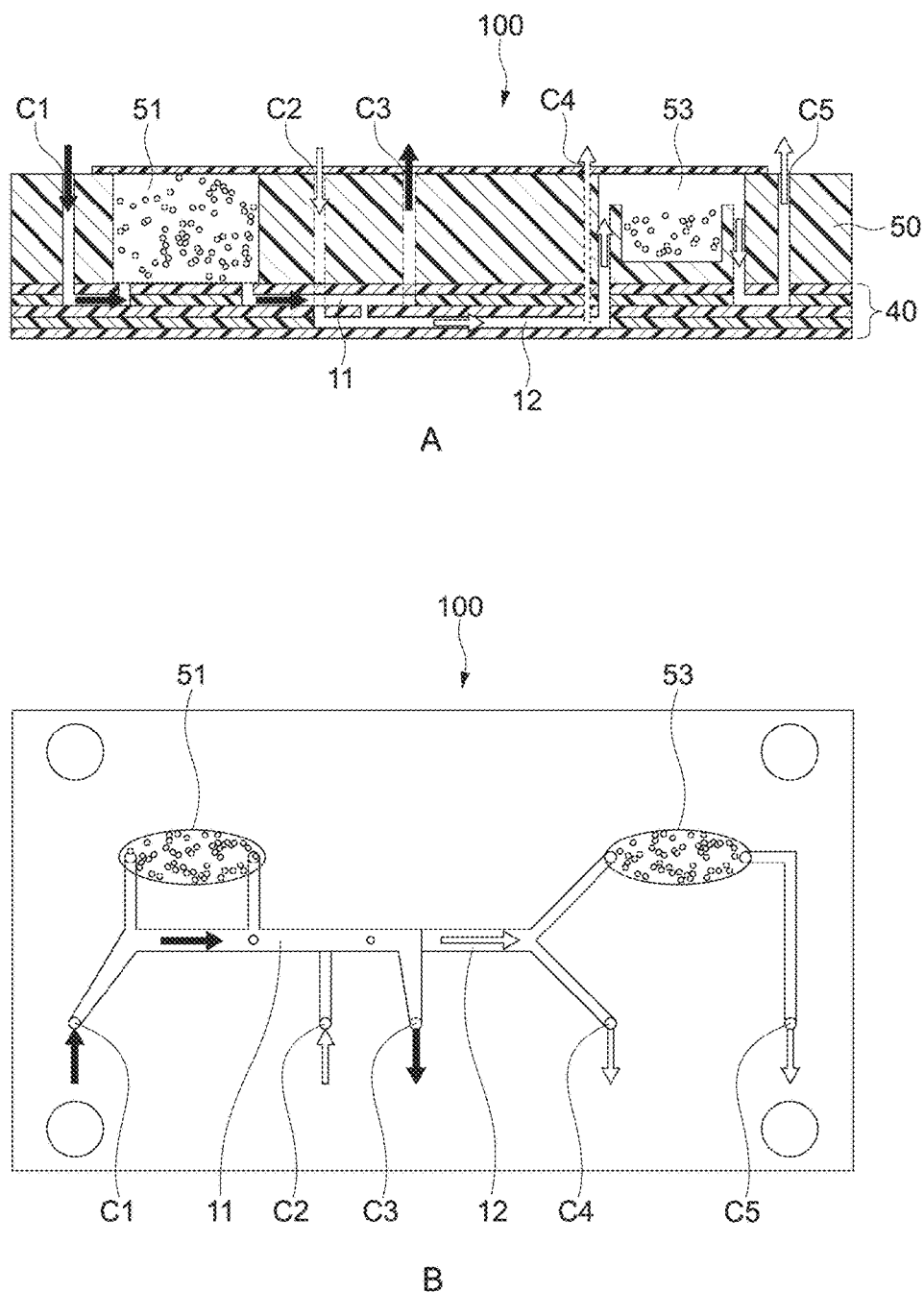
FIGS. 17A and 17B are diagrams for explaining a method of releasing clogging of particles in the vicinity of a narrowing channel.

It should be noted that when the particles block the narrowing channel K or the flow channel in the vicinity thereof to block the flow channel during the operation of the flow channel device 100 as shown in FIGS. 14A and 14B, the flow control mechanism 76 can temporarily open the port C3 to release the blocking as shown in FIGS. 17A and 17B. The blocking by the particles can be detected by measuring the electrical amount by the electrical means described above, that is, the processing section 70, in the vicinity of the narrowing channel K. When the particles are stuck in the vicinity of the narrowing channel K, the processing section 70 can detect the blocking by the particles since a resistance value higher than normal is continuously obtained.

Not only by the electrical means but also by an optical means such as photographing of the vicinity of the narrowing channel K by a camera and an analysis of reflected light or scattering light in the vicinity of the narrowing channel K caused by a light irradiation, the blocking by the particles can be detected.

As described above, in the flow channel device 100 of this embodiment, since the flow channel layer 40 is bonded to the vessel layer 50 and the injection vessel section 51 and the collection vessel section 53 are provided in the same vessel layer 50, the injection and collection of the fluid including the samples become easy, and workability is improved.

Further, since the inlet ports C1 and C2 and the outlet ports C3 to C5 leading to the flow control mechanism 76 are provided in the front surface of the vessel layer 50, the operator can easily perform a mechanical connection task of the flow control mechanism 76 and the flow channel device 100.

The vessel for injecting or collecting samples is created individually or created separate from the device constituting the flow channel in general. However, in the flow channel device 100, the injection vessel section 51, the flow channels of the flow channel layer 40, and the collection vessel section 53 are structured integrally, and the injection to the collection of samples are completed in a single flow channel device 100. This means that there is no path such as pipes and vessels to be shared with samples extracted by other people in the path from the injection to collection of samples. Therefore, the collected samples can be reused (e.g., re-cultivation and re-administration to living body), thus contributing to the field of Regenerative Medicine.

Furthermore, since contamination does not occur as described above, there is no need to clean and disinfect the flow channel device 100 as before, and time and costs can be saved to that extent. It is of course possible to clean and disinfect the flow channel device 100 to reuse the flow channel device 100.

As compared to a flow cytometer of the related art that uses an Eppendorf tube or the like for collection, the samples are not wasted, and the samples can be collected in a high concentration state.

When the materials as the base materials of the films P1 to P5 and the vessel layer 50 of this embodiment are the same polyimide material, for example, there is no need for an adhesive for the layers. Therefore, even when a fluid including biological samples flows through the flow channel of the flow channel device 100, damage due to an adhesive is not imparted to the biological samples. Furthermore, since polyimide is highly resistant to chemicals, not only a normal saline solution but also alcohols, an organic solvent, acid, and the like can be used as the fluid.

Since there is no need to use an adhesive and a polyimide film is used, the chemical resistance and heat resistance become high. Since the heat resistance becomes high, for example, high-pressure steam sterilization becomes possible for each flow channel device 100. Alternatively, since the heat resistance becomes high, a flow channel device having a structure of a basic concept according to the present technique (flow channel layer 40 and vessel layer 50) can also be applied to a chemical synthesis including a reaction, a fuel battery, and the like.

4. Other Embodiments

The present technique is not limited to the embodiment described above, and various other embodiments can also be realized.

In the vessel layer 50 of the embodiment above, the injection vessel section 51 is formed as a through hole, and the collection vessel section 53 is formed as a concave section. However, the injection vessel section 51 may be a concave section, and the collection vessel section 53 may be a through hole, or both of them may be a concave section or a through hole.

The vessel layer 50 is formed by molding in the embodiment above, but the vessel layer 50 may be formed by laminating films like the flow channel layer 40.

Although cells are exemplified as the biological samples in the embodiment above, DNA, proteins, and the like may be used instead. The samples are not limited to the biological samples, and other substances or materials may also be used.

The flow channel device 100 of the embodiment above includes the measurement electrode section 25 and is used by the analysis apparatus 200 that performs an electrical measurement of measuring an electrical amount of the fluid including particles in the narrowing channel K. However, the analysis apparatus may be an apparatus that optically analyzes it. In this case, the analysis apparatus only needs to include a light irradiation section that irradiates light (e.g., laser light) onto a sample that passes a predetermined position of a flow channel device and a detection section that detects at least one of fluorescent light and scattering light emitted from the sample due to the light irradiation. The applicant currently produces and sells an optical spectrum-type cell analyzer to which the present technique is applicable.

At least two of the feature portions of the embodiments described above can be combined.

The present technique may also take the following structures.

(1) A flow channel device, including:
a vessel layer including an injection vessel section into which a fluid including a sample is injected and a collection vessel section that collects the fluid; and
a flow channel layer that includes a flow channel connected to the injection vessel section and the collection vessel section and is bonded to the vessel layer.

(2) The flow channel device according to (1),
in which the injection vessel section is formed by a through hole provided in the vessel layer while using a surface of the flow channel layer as a bottom or includes a concave section provided in the vessel layer.

(3) The flow channel device according to (1),
in which the collection vessel section is formed by a through hole provided in the vessel layer while using a surface of the flow channel layer as a bottom or includes a concave section provided in the vessel layer.

(4) The flow channel device according to (3),
in which the collection vessel section includes
a concave accumulation section provided in the through hole or the concave section, and
a collection vessel inflow channel connected to an outside area of the accumulation section in the through hole or the concave section.

(5) The flow channel device according to (4),
in which the flow channel of the flow channel layer further includes a collection vessel outflow channel that opposes the collection vessel inflow channel and is connected to the flow channel.

(6) The flow channel device according to (1), in which:
the vessel layer includes a first inflow channel of a fluid not including the sample, the first inflow channel communicating an outside of the flow channel device and the flow channel of the flow channel layer with each other; and
the flow channel of the flow channel layer includes a first flow channel connected to the first inflow channel, and an injection vessel inflow channel and an injection vessel outflow channel that are branched from the first flow channel and connected to the injection vessel section.

(7) The flow channel device according to (6),
in which the injection vessel outflow channel has a smaller flow channel cross-sectional area than the first flow channel and is connected to the first flow channel at a center position of a width of the first flow channel in a direction orthogonal to a flowing direction of the fluid.

(8) The flow channel device according to (6) or (7),
in which the flow channel of the flow channel layer includes a narrowing channel and a second flow channel that is connected to the first flow channel via the narrowing channel and the collection vessel section.

(9) The flow channel device according to (8), in which the vessel layer includes a second inflow channel connected to the second flow channel.

(10) The flow channel device according to any one of (6) to (9),
in which the vessel layer includes an outflow channel that communicates the first flow channel and the outside of the flow channel device with each other.

(11) The flow channel device according to any one of (8) to (10), in which:
the second flow channel of the flow channel layer includes a plurality of branched branch channels; and
one of the plurality of branch channels is connected to the collection vessel section.

(12) The flow channel device according to any one of (8) to (11),
in which the flow channel layer includes an electrode pair provided in the flow channel while sandwiching the narrowing channel.

(13) The flow channel device according to (11) or (12),
in which the flow channel layer includes an operation electrode section that is provided between the narrowing channel and the plurality of branch channels in the second flow channel and applies an electrophoretic force to the sample.

(14) The flow channel device according to (1), in which:
the vessel layer includes a first inflow channel and a second inflow channel for a fluid not including the sample, the first inflow channel and the second inflow channel communicating an outside of the flow channel device and the flow channel of the flow channel layer with each other;
the flow channel of the flow channel layer includes a first flow channel connected to the first inflow channel and a second flow channel connected to the second inflow channel; and
the vessel layer includes a first outflow channel that communicates the first flow channel and the outside of the flow channel device with each other and a second outflow channel that communicates the second flow channel and the outside of the flow channel device with each other.

(15) The flow channel device according to any one of (1) to (14), further including
a film-like seal member that is provided above the injection vessel section and the collection vessel section of the vessel layer.

(16) The flow channel device according to any one of (1) to (15), further including
a valve provided between the injection vessel section and the flow channel of the flow channel layer.

(17) The flow channel device according to (16),
in which the valve is a water-soluble seal member.

(18) An analysis apparatus, including:
a flow channel device including
a vessel layer including an injection vessel section into which a fluid including a sample is injected and a collection vessel section that collects the fluid, and
a flow channel layer that includes a flow channel connected to the injection vessel section and the collection vessel section and an electrode section provided at a predetermined position of the flow channel and is bonded to the vessel layer; and
an apparatus including
a signal generation section configured to cause the electrode section to generate a voltage signal, and
a measurement section configured to measure an electrical amount at the predetermined position when the sample passes the predetermined position.

(19) An analysis apparatus, including:
a flow channel device including
a vessel layer including an injection vessel section into which a fluid including a sample is injected and a collection vessel section that collects the fluid, and
a flow channel layer that includes a flow channel connected to the injection vessel section and the collection vessel section and is bonded to the vessel layer;
a light irradiation section capable of irradiating light onto the sample that passes a predetermined position of the flow channel of the flow channel layer; and
a detection section that detects at least one of fluorescent light and scattering light emitted from the sample due to the irradiation of light.

(20) A fluid apparatus, including:
a flow channel device including a vessel layer including an injection vessel section into which a fluid including a sample is injected and a collection vessel section that collects the fluid, and a flow channel layer that includes a flow channel connected to the injection vessel section and the collection vessel section, an inlet of the flow channel, and an outlet of the flow channel and is bonded to the vessel layer; and a flow control mechanism that is connected to each of the inlet and the outlet of the flow channel and controls a flow of the fluid flowing in the flow channel.

(21) The fluid apparatus according to (20), in which:

the vessel layer includes a first inflow channel and a second inflow channel for a fluid not including the sample, the first inflow channel and the second inflow channel communicating an outside of the flow channel device and the flow channel of the flow channel layer with each other;

the flow channel of the flow channel layer includes a first flow channel connected to the first inflow channel and a second flow channel connected to the second inflow channel; and the vessel layer includes a first outflow channel that communicates the first flow channel and the outside of the flow channel device with each other and a second outflow channel that communicates the second flow channel and the outside of the flow channel device with each other.

DESCRIPTION OF SYMBOLS

S1 seal member
S2 valve
P1-P5 film
11 first flow channel
12 second flow channel
13 injection vessel inflow channel
15 injection vessel outflow channel
16, 17 branch channel
25 measurement electrode section
29 operation electrode section
40 flow channel layer
50 vessel layer
51 injection vessel section
53 collection vessel section
53a accumulation section
54 collection vessel inflow channel
55 collection vessel outflow channel
56 first inflow channel
57 first outflow channel
58 second inflow channel
59 outflow channel (second outflow channel)
70 processing section
76 flow control mechanism
100 flow channel device
200 analysis apparatus

The invention claimed is:

1. A flow channel device, comprising:
a vessel layer including an injection vessel section into which a fluid including a sample is injected and a collection vessel section that collects the fluid; and
a flow channel layer that includes a flow channel connected to the injection vessel section and the collection vessel section and is bonded to the vessel layer, wherein:
the vessel layer includes a first inflow channel, the first inflow channel communicating with the flow channel of the flow channel layer;
the flow channel of the flow channel layer includes a first flow channel connected to the first inflow channel, and includes an injection vessel inflow channel and an injection vessel outflow channel that are branched from the first flow channel and connected to the injection vessel section;
the injection vessel outflow channel has a smaller flow channel cross-sectional area than the first flow channel and is connected to the first flow channel at a center position of a width of the first flow channel in a direction orthogonal to a flowing direction of the fluid;
the collection vessel section includes a through hole in the vessel layer and a concave member located in the through hole, the concave member having a concave accumulation region and having a depth less than a depth of the through hole in the vessel layer, thereby defining a shallow area of the collection vessel section above the concave member; and
the flow channel is connected to the shallow area of the collection vessel section.

2. The flow channel device according to claim 1, wherein the injection vessel section is formed by a through hole provided in the vessel layer, with a surface of the flow channel layer as a bottom, or by a concave member provided in the vessel layer.

3. The flow channel device according to claim 1, wherein the collection vessel section includes
a concave accumulation member, and
a collection vessel inflow channel connected to an area outside of the concave accumulation member.

4. The flow channel device according to claim 3, wherein the flow channel of the flow channel layer further includes a collection vessel outflow channel that opposes the collection vessel inflow channel and is connected to the flow channel.

5. The flow channel device according to claim 1, wherein the flow channel of the flow channel layer includes a narrowing channel and a second flow channel that is connected to the first flow channel via the narrowing channel and the collection vessel section.

6. The flow channel device according to claim 5, wherein the vessel layer includes a second inflow channel connected to the second flow channel.

7. The flow channel device according to claim 5, wherein:
the second flow channel of the flow channel layer includes a plurality of branched branch channels; and
one of the plurality of branch channels is connected to the collection vessel section.

8. The flow channel device according to claim 7, wherein the flow channel layer includes an operation electrode section that is provided between the narrowing channel and the plurality of branch channels in the second flow channel and applies an electrophoretic force to the sample.

9. The flow channel device according to claim 5, wherein the flow channel layer includes an electrode pair provided in the flow channel while sandwiching the narrowing channel.

10. The flow channel device according to claim 1, wherein the vessel layer includes an outflow channel that communicates with the first flow channel.

11. The flow channel device according to claim 1, wherein:
the vessel layer includes a first inflow channel and a second inflow channel, the first inflow channel and the second inflow channel communicating with the flow channel of the flow channel layer;

the flow channel of the flow channel layer includes a first flow channel connected to the first inflow channel and a second flow channel connected to the second inflow channel; and the vessel layer includes a first outflow channel that communicates with the first flow channel and a second outflow channel that communicates with the second flow channel.

12. The flow channel device according to claim 1, further comprising a seal member that is provided above the injection vessel section and the collection vessel section of the vessel layer.

13. The flow channel device according to claim 1, further comprising a valve provided between the injection vessel section and the flow channel of the flow channel layer.

14. The flow channel device according to claim 13, wherein the valve is a water-soluble seal member.

* * * * *